US009994876B2

(12) United States Patent
Stephanopoulos et al.

(10) Patent No.: US 9,994,876 B2
(45) Date of Patent: Jun. 12, 2018

(54) ENGINEERING MICROBES AND METABOLIC PATHWAYS FOR THE PRODUCTION OF ETHYLENE GLYCOL

(71) Applicant: Massachusetts Institute of Technology, Cambridge, MA (US)

(72) Inventors: Gregory Stephanopoulos, Winchester, MA (US); Brian Pereira, Cambridge, MA (US); Marjan De Mey, Ghent (BE); Deepak Dugar, Cambridge, MA (US); Jose Luis Avalos, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days. days.

(21) Appl. No.: 14/864,493

(22) Filed: Sep. 24, 2015

(65) Prior Publication Data
US 2016/0076061 A1    Mar. 17, 2016

Related U.S. Application Data

(63) Continuation of application No. 13/774,212, filed on Feb. 22, 2013, now abandoned.

(60) Provisional application No. 61/602,322, filed on Feb. 23, 2012.

(51) Int. Cl.
| *C12P 7/24*  | (2006.01) |
| *C12P 7/18*  | (2006.01) |
| *C12N 1/21*  | (2006.01) |
| *C12N 15/52* | (2006.01) |
| *C12N 9/02*  | (2006.01) |
| *C12N 9/04*  | (2006.01) |
| *C12N 9/06*  | (2006.01) |
| *C12N 9/10*  | (2006.01) |
| *C12N 9/12*  | (2006.01) |
| *C12N 9/16*  | (2006.01) |
| *C12N 9/90*  | (2006.01) |
| *C12N 9/88*  | (2006.01) |
| *C12N 15/70* | (2006.01) |

(52) U.S. Cl.
CPC .............. *C12P 7/24* (2013.01); *C12N 9/0006* (2013.01); *C12N 9/0008* (2013.01); *C12N 9/0022* (2013.01); *C12N 9/1096* (2013.01); *C12N 9/1205* (2013.01); *C12N 9/1229* (2013.01); *C12N 9/16* (2013.01); *C12N 9/88* (2013.01); *C12N 9/90* (2013.01); *C12N 15/52* (2013.01); *C12N 15/70* (2013.01); *C12P 7/18* (2013.01); *C12Y 101/01071* (2013.01); *C12Y 102/01052* (2013.01); *C12Y 207/01016* (2013.01); *C12Y 207/01047* (2013.01); *C12Y 401/02017* (2013.01); *C12Y 501/03* (2013.01);

*C12P 2203/00* (2013.01); *C12Y 102/01021* (2013.01); *C12Y 207/01017* (2013.01)

(58) Field of Classification Search
None
See application file for complete search history.

(56) References Cited

U.S. PATENT DOCUMENTS

| 6,037,154 A      | 3/2000  | Suga et al.      |              |
| 7,371,558 B2     | 5/2008  | Cervin et al.    |              |
| 7,732,176 B2     | 6/2010  | Eggeling et al.  |              |
| 8,383,377 B2 *   | 2/2013  | Yanase ............ | C12N 9/1022 |
|                  |         |                  | 435/161      |
| 2009/0325245 A1  | 12/2009 | Soucaille et al. |              |
| 2011/0076730 A1  | 3/2011  | Frost et al.     |              |
| 2011/0294178 A1  | 12/2011 | Soucaille et al. |              |
| 2011/0312049 A1  | 12/2011 | Osterhout et al. |              |
| 2013/0217070 A1* | 8/2013  | Zhao ............. | C12P 19/00   |
|                  |         |                  | 435/72       |
| 2013/0316416 A1  | 11/2013 | Stephanopoulos et al. |       |

FOREIGN PATENT DOCUMENTS

| FR |           3028529 A1 * | 5/2016  | ............... C12P 7/18 |
| WO | WO 2008091288 A2 *     | 7/2008  | ........... C12N 9/0006   |
| WO | WO 2010/076324 A1      | 7/2010  |                           |
| WO | WO 2011/130378 A1      | 10/2011 |                           |

OTHER PUBLICATIONS

Jeffries, Engineering yeast for xylose metabolism, Curr. Opin. Biotechnol., 2006, 17, 320-26.*
Van Maris et al., Development of Efficient Xylose Fermentation in *Saccharomyces cerevisiae*: Xylose Isomerase as a Key Component, Adv. Biochem. Engin/Biotechnol, 2007, 108, 179-204.*
PCT/US2013/027351, May 10, 2013, International Search Report and Written Opinion.
PCT/US2013/027351, Sep. 4, 2014, International Preliminary Report on Patentability.
UNIPROT Submission. Acession No. P46883. 2011.
Ajikumar et al., Isoprenoid pathway optimization for Taxol precursor overproduction in *Escherichia coli*. Science. Oct. 1, 2010;330(6000):70-4. doi: 10.1126/science.1191652.
Anderson et al., Human neutrophils employ the myeloperoxidase-hydrogen peroxide-chloride system to convert hydroxy-amino acids into glycolaldehyde, 2-hydroxypropanal, and acrolein. A mechanism for the generation of highly reactive alpha-hydroxy and alpha,beta-unsaturated aldehydes by phagocytes at sites of inflammation. J Clin Invest. Feb. 1, 1997;99(3):424-32.
Badia et al., L-lyxose metabolism employs the L-rhamnose pathway in mutant cells of *Escherichia coli* adapted to grow on L-lyxose. J Bacteriol. Aug. 1991;173(16):5144-50.
Baldoma et al., Involvement of lactaldehyde dehydrogenase in several metabolic pathways of *Escherichia coli* K12. J Biol Chem. Oct. 15, 1987;262(29):13991-6.

(Continued)

Primary Examiner — Robert B Mondesi
Assistant Examiner — Todd M Epstein
(74) Attorney, Agent, or Firm — Wolf, Greenfield & Sacks, P.C.

(57) ABSTRACT

The invention relates to recombinant cells and their use in the production of ethylene glycol.

26 Claims, 10 Drawing Sheets

(56) References Cited

OTHER PUBLICATIONS

Chiu et al., L-Rhamnulose-1-phosphate aldolase. Meth in Enzymol. 1975;42:264-9.
Davies et al., The enzymatic decarboxylation of hydroxypyruvate associated with purified pyruvate decarboxylase from wheat germ. Phytochemistry. 1985;24(2):231-4.
Hedrick et al., The metabolism of hydroxypyruvate. I. The nonenzymatic decarboxylation and autoxddation of hydroxypyruvate. J Biol Chem. Jul. 1961;236:1867-71.
Hedrick et al., The nonoxidative decarboxylation of hydroxypyruvate in mammalian systems. Arch Biochem Biophys. May 1964;105:261-9.
Helanto et al., Metabolic engineering of Lactobacillus plantarum for production of L-ribulose. Appl Environ Microbiol. Nov. 2007;73(21):7083-91. Epub Sep. 14, 2007.
Izumori et al., A New Enzyme, D-Ketohexose 3-Epimerase, from *Pseudomonas* sp. ST-24. Biosci Biotech Biochem. 1993;57(6):1037-9.
Kulkarni et al., Ethanolamine oxidase from the blowfly, *Phormia regina* (Diptera: Insecta). Comp Biochem Physiol B. Feb. 15, 1973;44(2):407-22.
Limón et al., The aldA gene of *Escherichia coli* is under the control of at least three transcriptional regulators. Microbiology. Jun. 1997;143 ( Pt 6):2085-95.
Ota et al., Enzymatic characterization of an amine oxidase from *Arthrobacter* sp. used to measure phosphatidylethanolamine. Biosci Biotechnol Biochem. Oct. 2008;72(10):2732-8. Epub Oct. 7, 2008.
Pace et al., A molecular view of microbial diversity and the biosphere. Science. May 2, 1997;276(5313):734-40.
Parsons et al., Crystal structure of a quinoenzyme: copper amine oxidase of *Escherichia coli* at 2 A resolution. Structure. Nov. 15, 1995;3(11):1171-84.
Rontein et al., Plants synthesize ethanolamine by direct decarboxylation of serine using a pyridoxal phosphate enzyme. J Biol Chem. Sep. 21, 2001;276(38):35523-9. Epub Jul. 18, 2001.

\* cited by examiner

ENGINEERING MICROBES AND METABOLIC PATHWAYS FOR THE PRODUCTION OF ETHYLENE GLYCOL

RELATED APPLICATIONS

This application is a continuation of U.S. patent application Ser. No. 13/774,212, filed Feb. 22, 2013, which claims the benefit under 35 U.S.C. § 119(e) of U.S. provisional application No. 61/602,322, filed Feb. 23, 2012, each of which is incorporated by reference herein in its entirety.

GOVERNMENT INTEREST

This invention was made with government support under Grant No. DE-AR0000059 awarded by the Department of Energy, Office of ARPA-E. The government has certain rights in this invention.

FIELD OF THE INVENTION

The invention relates to the production of ethylene glycol through recombinant gene expression and metabolic engineering.

BACKGROUND OF THE INVENTION

Ethylene glycol is an important organic compound commonly used as a precursor to polymers, primarily polyethylene terephthalate (PET) which comprises a significant share of the world's polymer production. The major end uses of PET are synthetic fibers, commonly referred to as "polyester," and plastic bottles. For both of these products, the demand is increasing. Another major use of ethylene glycol is as a coolant such as automotive antifreeze. Though less significant, there are also several other uses for ethylene glycol.

Currently, ethylene glycol is primarily generated from ethylene oxide which is derived from fossil fuels. With the growing issues surrounding fossil fuels, generating ethylene glycol from renewable sources provides a potential alternative. Thus, ethylene glycol also is chemically produced from plant-derived ethanol. However, the direct biological production of ethylene glycol from renewable sources had not been exhibited.

SUMMARY OF THE INVENTION

The present invention is based, at least in part, on the discovery that ethylene glycol can be produced directly from renewable resources. Of biological sources for the generation of ethylene glycol, lignocellulosic biomass is the most abundant and very promising. The cellulose and hemicellulose fractions of lignocellulose, or other sources of sugars including algae, can be broken down into their monosaccharide units, primarily glucose, xylose and other pentoses. Additionally, the production of biodiesel results in significant amounts of waste glycerol, a sugar alcohol which can be used as a substrate. Our research shows that by using engineered microbes we can convert these simple sugars and glycerol into ethylene glycol.

According to one aspect, cells engineered to produce ethylene glycol are provided. The cells in some embodiments have reduced or eliminated activity or expression of aldehyde dehydrogenase A relative to a wild type cell. In some embodiments, the aldehyde dehydrogenase A is encoded by an aldA gene, and the cell includes a deletion of the aldA gene. This may be referred to herein as ΔaldA.

In some embodiments, the cells have reduced or eliminated activity or expression of xylulokinase relative to wild type cells. In some embodiments, the xylulokinase is encoded by a xylB gene, and the cells include a deletion of the xylB gene. This may be referred to herein as ΔxylB.

In some embodiments, the cells have reduced or eliminated activity or expression of L-ribulokinase relative to wild type cells. In some embodiments, the L-ribulokinase is encoded by an araB gene, and the cells include a deletion of the araB gene. This may be referred to herein as ΔaraB.

As will be understood by persons skilled in the art, the activity or expression of aldehyde dehydrogenase A and/or xylulokinase and/or L-ribulokinase in the cells can be reduced, attenuated or eliminated in several ways, including by reducing expression of the relevant gene(s), disrupting the relevant gene(s), introducing mutation(s) in the relevant gene(s) that results in production of a protein with reduced, attenuated or eliminated enzymatic activity, use of specific enzyme inhibitors to reduce, attenuate or eliminate the enzymatic activity, etc.

In some embodiments, the cells recombinantly express an enzyme that interconverts D-xylulose and D-ribulose. In some embodiments, the cells recombinantly express an enzyme that interconverts L-ribulose and L-xylulose. In some embodiments, the enzyme that interconverts D-xylulose and D-ribulose and/or L-ribulose and L-xylulose, is D-tagatose 3-epimerase (also referred to herein as DTE). In some embodiments, the DTE is encoded by a gene referred to herein as dte. In some embodiments, the dte gene is from *Pseudomonas cichorii*. In some embodiments, the cells overexpress a dte gene.

In some embodiments, the cells recombinantly express D-ribulokinase, D-ribulose-phosphate aldolase and glycolaldehyde reductase. In some embodiments, the D-ribulokinase is encoded by a fucK gene and/or the D-ribulose-phosphate aldolase is encoded by a fucA gene and/or the glycolaldehyde reductase is encoded by a fucO gene. In some embodiments, the cells overexpress the fucK gene and/or the fucA gene and/or the fucO gene. In some embodiments, the fucK gene, the fucA gene and the fucO gene are expressed as part of an operon in conjunction with a dte gene. In some embodiments, the order of the genes in the operon is dte-fucA-fucO-fucK.

In some embodiments, the cells recombinantly express ATP:L-xylulose 1-phosphotransferase, L-xylulose-1-phosphate aldolase, and glycolaldehyde reductase. In some embodiments, the ATP:L-xylulose 1-phosphotransferase is encoded by a rhaB gene and/or the L-xylulose-1-phosphate aldolase is encoded by a rhaD gene and/or the glycolaldehyde reductase is encoded by a fucO gene. In some embodiments, the cells overexpress the rhaB gene and/or the rhaD gene and/or the fucO gene. In some embodiments, the rhaB gene, the rhaD gene and the fucO gene are expressed as part of an operon in conjunction with a dte gene. In some embodiments, the order of the genes in the operon is dte-rhaB-rhaD fucO.

In some embodiments, the cells express a subunit of the E1 component of 2-oxoglutarate dehydrogenase within ΔaldA ΔxylB. In some embodiments, the subunit of the E1 component of 2-oxoglutarate dehydrogenase is encoded by a sucA gene. In some embodiments, the cells overexpress a sucA gene.

In some embodiments, the cells are bacterial cells, fungal cells (including yeast cells), plant cells, insect cells or animal cells. In some embodiments, the cells are bacterial cells such as, for example, *Escherichia coli* (*E. coli*) cells.

In some embodiments, the cells endogenously express the gene encoding D-ribulokinase, D-ribulose-phosphate aldolase, glycolaldehyde reductase, ATP:L-xylulose 1-phosphotransferase, L-xylulose-1-phosphate aldolase, and/or a subunit of the E1 component of 2-oxoglutarate dehydrogenase; in such embodiments, endogenous expression of the gene encoding D-ribulokinase, D-ribulose-phosphate aldolase, glycolaldehyde reductase, ATP:L-xylulose 1-phosphotransferase, L-xylulose-1-phosphate aldolase, and/or subunit of the E1 component of 2-oxoglutarate dehydrogenase is increased through modification of the gene(s) and/or their promoter(s) and/or their ribosome binding sites (RBSs). In some embodiments, the gene encoding D-ribulokinase, D-ribulose-phosphate aldolase, glycolaldehyde reductase, ATP:L-xylulose 1-phosphotransferase, L-xylulose-1-phosphate aldolase, and/or a subunit of the E1 component of 2-oxoglutarate dehydrogenase is expressed from a plasmid. In some embodiments, one or more copies of the gene encoding D-ribulokinase, D-ribulose-phosphate aldolase, glycolaldehyde reductase, ATP:L-xylulose 1-phosphotransferase, L-xylulose-1-phosphate aldolase, and/or a subunit of the E1 component of 2-oxoglutarate dehydrogenase is integrated into the genome of the cells.

In some embodiments, the cells recombinantly express a 3-phosphoglycerate dehydrogenase. In some embodiments, the 3-phosphoglycerate dehydrogenase is a mutant resistant to inhibition by serine. In some embodiments, the 3-phosphoglycerate dehydrogenase is encoded by a serA gene of *E. coli*.

In some embodiments, the cells recombinantly express a glycerate kinase. In some embodiments, the glycerate kinase is a glycerate kinase II encoded by a glxK gene of *E. coli*, or a glycerate kinase I encoded by a garK gene of *E. coli*.

In some embodiments, the expression or activity in the cells of one or more phosphoglycerate mutases and/or of enolase is attenuated, thereby increasing the amount of 3-phosphoglycerate in the cell by reducing flux to 2-phosphoglycerate and/or increasing the amount of 2-phophoglycerate in the cell by reducing flux to phosphoenolpyruvate. In some embodiments, the one or more phosphoglycerate mutases is encoded by gpmA, gpmB, and gpmM genes of *E. coli* and/or the enolase is encoded by an eno gene from *E. coli*.

In some embodiments, the cells recombinantly express a 3-phosphoserine aminotransferase to convert 3-phosphohydroxypyruvate to 3-phospho-L-serine and optionally further recombinantly express a phosphoserine phosphatase to convert 3-phospho-L-serine to L-serine. In some embodiments, the 3-phosphoserine aminotransferase and phosphoserine phosphatase are encoded by serC and serB genes of *E. coli*, respectively.

In some embodiments, the expression or activity in the cells of one or more serine deaminases is attenuated. In some embodiments, the one or more serine deaminases is encoded by sdaA, sdaB, tdcB, and tdcG genes of *E. coli*.

In some embodiments, the cells recombinantly express a serine decarboxylase and ethanolamine oxidae. In some embodiments, the serine decarboxylase is encoded by a gene from *Arabidopsis thaliana* (referred to as sdc), and the ethanolamine oxidase is encoded by a gene from *Arthrobacter* sp (referred to as aao). In some embodiments, the serine decarboxylase gene from *A. thaliana* is truncated (referred to as t-sdc).

In some embodiments, the cells recombinantly express a 3-phosphohydroxypyruvate phosphatase. In some embodiments, the 3-phosphohydroxypyruvate phosphatase is encoded by a yeaB gene of *E. coli* or by GPP2 of *S. cerevisiae*.

In some embodiments, the cells recombinantly express a serine:pyruvate aminotransferase (SPT) and/or an alanine:glyoxylate aminotransferase (AGT). In some embodiments, the SPT and/or the AGT is encoded by a gene of *Arabidopsis thaliana, Drosophila melanogaster, Canis lupus familiaris, Homo sapiens* and/or *Rattus norvegicus*.

According to another aspect, methods for producing ethylene glycol are provided. The methods include culturing any of the cells described herein to produce ethylene glycol.

In some embodiments, the cells are cultured in minimal medium supplemented with a carbon source. In some embodiments, the carbon source includes D-arabinose and/or L-arabinose and/or D-glucose and/or glycerol and/or D-xylose and/or a biomass hydrolysate and/or L-arabinose and/or glycerol and/or serine.

In some embodiments, the cells are cultured aerobically. In other embodiments, the cell is cultured anaerobically.

In some embodiments, the methods further include recovering the ethylene glycol from the cell culture and/or culture supernatants.

In some embodiments, at least 1 g/L ethylene glycol is produced. In some embodiments, at least 10 g/L ethylene glycol is produced.

According to another aspect, cell cultures are provided. The cell cultures are produced by culturing any of the cells described herein or by culturing any of the cells described herein according to any of the methods described herein.

In some embodiments, the cell culture contains at least 1 g/L ethylene glycol. In some embodiments, the cell culture contains at least 10 g/L ethylene glycol.

According to another aspect, supernatants of a cell culture are provided. The supernatants are produced by culturing any of the cells described herein or by culturing any of the cells described herein according to any of the methods described herein.

In some embodiments, the supernatants contain at least 1 g/L ethylene glycol. In some embodiments, the supernatants contain at least 10 g/L ethylene glycol.

According to another aspect, methods for producing ethylene glycol in cells are provided. The methods include reducing or eliminating the activity or expression of aldehyde dehydrogenase A and/or xylulokinase in the cells, relative to wild type cells; increasing the expression of an enzyme that interconverts D-xylulose and D-ribulose, a D-ribulokinase, D-ribulose-phosphate aldolase, glycolaldehyde reductase and/or subunit of the E1 component of 2-oxoglutarate dehydrogenase in the cells, relative to wild type cells; and culturing the cells.

In some embodiments, the aldehyde dehydrogenase A is encoded by an aldA gene, and the cell comprises a deletion of the aldA gene ($\Delta$aldA). In certain embodiments, the xylulokinase is encoded by a xylB gene, and the cell comprises a deletion of the xylB gene ($\Delta$xylB).

In some embodiments, the enzyme that interconverts D-xylulose and D-ribulose is D-tagatose 3-epimerase (DTE). In certain embodiments, the DTE is encoded by a dte gene. In some embodiments, the dte gene is from *Pseudomonas cichorii*. In some embodiments, the cell overexpresses a dte gene.

In some embodiments, the D-ribulokinase is encoded by a fucK gene and/or the D-ribulose-phosphate aldolase is encoded by a fucA gene and/or the glycolaldehyde reductase is encoded by a fucO gene. In certain embodiments, the cell overexpresses the fucK gene and/or the fucA gene and/or the fucO gene. In some embodiments, the fucK gene, the fucA gene and the fucO gene are expressed as part of an operon in conjunction with a dte gene. In preferred embodiments, the order of the genes in the operon is dte-fucA-fucO-fucK.

In some embodiments, the cell expresses a subunit of the E1 component of 2-oxoglutarate dehydrogenase within ΔaldA ΔxylB. In certain embodiments, the subunit of the E1 component of 2-oxoglutarate dehydrogenase is encoded by a sucA gene. In some embodiments, the cell overexpresses a sucA gene.

In some embodiments, the cell recombinantly expresses a 3-phosphoglycerate dehydrogenase. In certain embodiments, the 3-phosphoglycerate dehydrogenase is encoded by a serA gene of *E. coli*.

In some embodiments, the cell recombinantly expresses a glycerate kinase. In certain embodiments, the glycerate kinase is a glycerate kinase II encoded by a glxK gene of *E. coli*, or a glycerate kinase I encoded by a garK gene of *E. coli*.

In some embodiments, the expression or activity in the cell of one or more phosphoglycerate mutases and/or of enolase is attenuated, thereby increasing the amount of 3-phosphoglycerate in the cell by reducing flux to 2-phosphoglycerate and/or increasing the amount of 2-phophoglycerate in the cell by reducing flux to phosphoenolpyruvate. In certain embodiments, the one or more phosphoglycerate mutases is encoded by gpmA, gpmB, and gpmM genes of *E. coli* and/or of enolase is encoded by an eno gene from *E. coli*.

In some embodiments, the cell recombinantly expresses a 3-phosphoserine aminotransferase to convert 3-phosphohydroxypyruvate to 3-phospho-L-serine and optionally further recombinantly expresses a phosphoserine phosphatase to convert 3-phospho-L-serine to L-serine. In certain embodiments, the 3-phosphoserine aminotransferase and phosphoserine phosphatase are encoded by serC and serB genes of *E. coli*, respectively.

In some embodiments, the expression or activity in the cell of one or more serine deaminases is attenuated. In certain embodiments, the one or more serine deaminases is encoded by sdaA, sdaB, tdcB, and tdcG genes of *E. coli*.

In some embodiments, the cell recombinantly expresses a serine decarboxylase.

In some embodiments, the cell recombinantly expresses a 3-phosphohydroxypyruvate phosphatase. In certain embodiments, the 3-phosphohydroxypyruvate phosphatase is encoded by a yeaB gene of *E. coli* or by GPP2 of *S. cerevisiae*.

In some embodiments, the cell recombinantly expresses a serine:pyruvate aminotransferase (SPT) and/or an alanine:glyoxylate aminotransferase (AGT). In certain embodiments, the SPT and/or AGT is encoded by a gene of *Arabidopsis thaliana, Drosophila melanogaster, Canis lupus familiaris, Homo sapiens*, and *Rattus norvegicus*.

In some embodiments, the cell is a bacterial cell, a fungal cell (including a yeast cell), a plant cell, an insect cell or an animal cell. In certain embodiments, the cell is a bacterial cell. In preferred embodiments, the bacterial cell is an *Escherichia coli* cell.

In some embodiments, the cell is cultured in minimal medium supplemented with a carbon source. In certain embodiments, the carbon source comprises D-arabinose and/or D-glucose and/or D-xylose and/or a biomass hydrolysate and/or L-arabinose and/or glycerol and/or serine.

In some embodiments, the cells are cultured in minimal medium supplemented with serine.

In some embodiments, the cell is cultured aerobically. In other embodiments, the cell is cultured anaerobically.

In some embodiments, the methods further include recovering the ethylene glycol from the cell culture and/or culture supernatants. In certain embodiments, at least 1 g/L ethylene glycol is produced. In preferred embodiments, at least 10 g/L ethylene glycol is produced.

According to yet another aspect, methods for producing ethylene glycol in cells include reducing or eliminating the activity or expression of aldehyde dehydrogenase A and/or L-ribulokinase in the cells, relative to wild type cells; increasing the expression of an enzyme that interconverts L-ribulose and L-xylulose, an ATP:L-xylulose 1-phosphotransferase, L-xylulose-1-phosphate aldolase, and glycolaldehyde reductase in the cells, relative to wild type cells; and culturing the cells.

In some embodiments, the aldehyde dehydrogenase A is encoded by an aldA gene, and wherein the cell comprises a deletion of the aldA gene (ΔaldA). In some embodiments, the L-ribulokinase is encoded by a araB gene, and wherein the cell comprises a deletion of the araB gene (ΔaraB).

In some embodiments, the enzyme that interconverts L-ribulose and L-xylulose is D-tagatose 3-epimerase (DTE). In some embodiments, the DTE is encoded by a dte gene. In some embodiments, the dte gene is from *Pseudomonas cichorii*. In some embodiments, the cell overexpresses a dte gene.

In some embodiments, the ATP:L-xylulose 1-phosphotransferase is encoded by a rhaB gene and/or the L-xylulose-1-phosphate aldolase is encoded by a rhaD gene and/or the glycolaldehyde reductase is encoded by a fucO gene. In some embodiments, the cell overexpresses the rhaB gene and/or the rhaD gene and/or the fucO gene. In some embodiments, the rhaB gene, the rhaD gene and the fucO gene are expressed as part of an operon in conjunction with a dte gene. In some embodiments, the order of the genes in the operon is dte-rhaB-rhaD-fucO.

In some embodiments, the cell recombinantly expresses a 3-phosphoglycerate dehydrogenase. In some embodiments, the 3-phosphoglycerate dehydrogenase is a mutant resistant to inhibition by serine. In some embodiments, the 3-phosphoglycerate dehydrogenase is encoded by a serA gene of *E. coli*.

In some embodiments, the cell recombinantly expresses a glycerate kinase. In some embodiments, the glycerate kinase is a glycerate kinase II encoded by a glxK gene of *E. coli*, or a glycerate kinase I encoded by a garK gene of *E. coli*.

In some embodiments, the expression or activity in the cell of one or more phosphoglycerate mutases and/or of enolase is attenuated, thereby increasing the amount of 3-phosphoglycerate in the cell by reducing flux to 2-phosphoglycerate and/or increasing the amount of 2-phophoglycerate in the cell by reducing flux to phosphoenolpyruvate. In some embodiments, one or more phosphoglycerate mutases is encoded by gpmA, gpmB, and gpmM genes of *E. coli* and/or of enolase is encoded by an eno gene from *E. coli*.

In some embodiments, the cell recombinantly expresses a 3-phosphoserine aminotransferase to convert 3-phosphohydroxypyruvate to 3-phospho-L-serine and optionally further recombinantly expresses a phosphoserine phosphatase to convert 3-phospho-L-serine to L-serine. In some embodiments, the 3-phosphoserine aminotransferase and phosphoserine phosphatase are encoded by serC and serB genes of *E. coli*, respectively.

In some embodiments, the expression or activity in the cell of one or more serine deaminases is attenuated. In some embodiments, one or more serine deaminases is encoded by sdaA, sdaB, tdcB, and tdcG genes of *E. coli*.

In some embodiments, the cell recombinantly expresses a serine decarboxylase and/or ethanolamine oxidase. In some embodiments, the serine decarboxylase is encoded by a gene from *Arabidopsis thaliana*, and the ethanolamine oxidase is encoded by a gene from *Arthrobacter* sp. In some embodiments, the gene from *Arabidopsis thaliana* is sdc, and the gene from *Arthrobacter* sp. is aao. In some embodiments, the serine decarboxylase gene from *A. thaliana* is truncated. In some embodiments, the gene from *A. thaliana* is t-sdc.

In some embodiments, the cell recombinantly expresses a 3-phosphohydroxypyruvate phosphatase. In some embodiments, the 3-phosphohydroxypyruvate phosphatase is encoded by a yeaB gene of *E. coli* or by GPP2 of *S. cerevisiae*.

In some embodiments, the cell recombinantly expresses a serine:pyruvate aminotransferase (SPT) and/or an alanine:glyoxylate aminotransferase (AGT). In some embodiments, the SPT and/or AGT is encoded by a gene of *Arabidopsis thaliana, Drosophila melanogaster, Canis lupus familiaris, Homo sapiens,* and *Rattus norvegicus*.

In some embodiments, the cell is a bacterial cell, a fungal cell (including a yeast cell), a plant cell, an insect cell or an animal cell. In some embodiments, the cell is a bacterial cell. In some embodiments, the bacterial cell is an *Escherichia coli* cell.

In some embodiments, the cell is cultured in minimal medium supplemented with a carbon source. In some embodiments, the carbon source comprises D-arabinose. In some embodiments, the carbon source comprises D-glucose. In some embodiments, the carbon source comprises D-xylose. In some embodiments, the carbon source comprises a biomass hydrolysate. In some embodiments, the carbon source comprises L-arabinose. In some embodiments, the carbon source comprises glycerol. In some embodiments, the carbon sources comprises serine.

In some embodiments, the cells are cultured in minimal medium supplemented with serine.

In some embodiments, the cell is cultured aerobically. In some embodiments, the cell is cultured anaerobically.

In some embodiments, the methods further comprise recovering the ethylene glycol from the cell culture and/or culture supernatants.

In some embodiments, at least 1 g/L ethylene glycol is produced. In some embodiments, at least 10 g/L ethylene glycol is produced. According to another aspect, a cell culture produced by any of the foregoing methods is provided. In some embodiments, the cell culture and/or culture supernatant contains at least 1 g/L ethylene glycol. In certain embodiments, the cell culture and/or culture supernatant contains at least 10 g/L ethylene glycol.

According to another aspect, a supernatant of a cell culture produced by any of the foregoing methods is provided.

These and other aspects of the invention are described further below.

DETAILED DESCRIPTION OF SOME EMBODIMENTS

Figure 1:
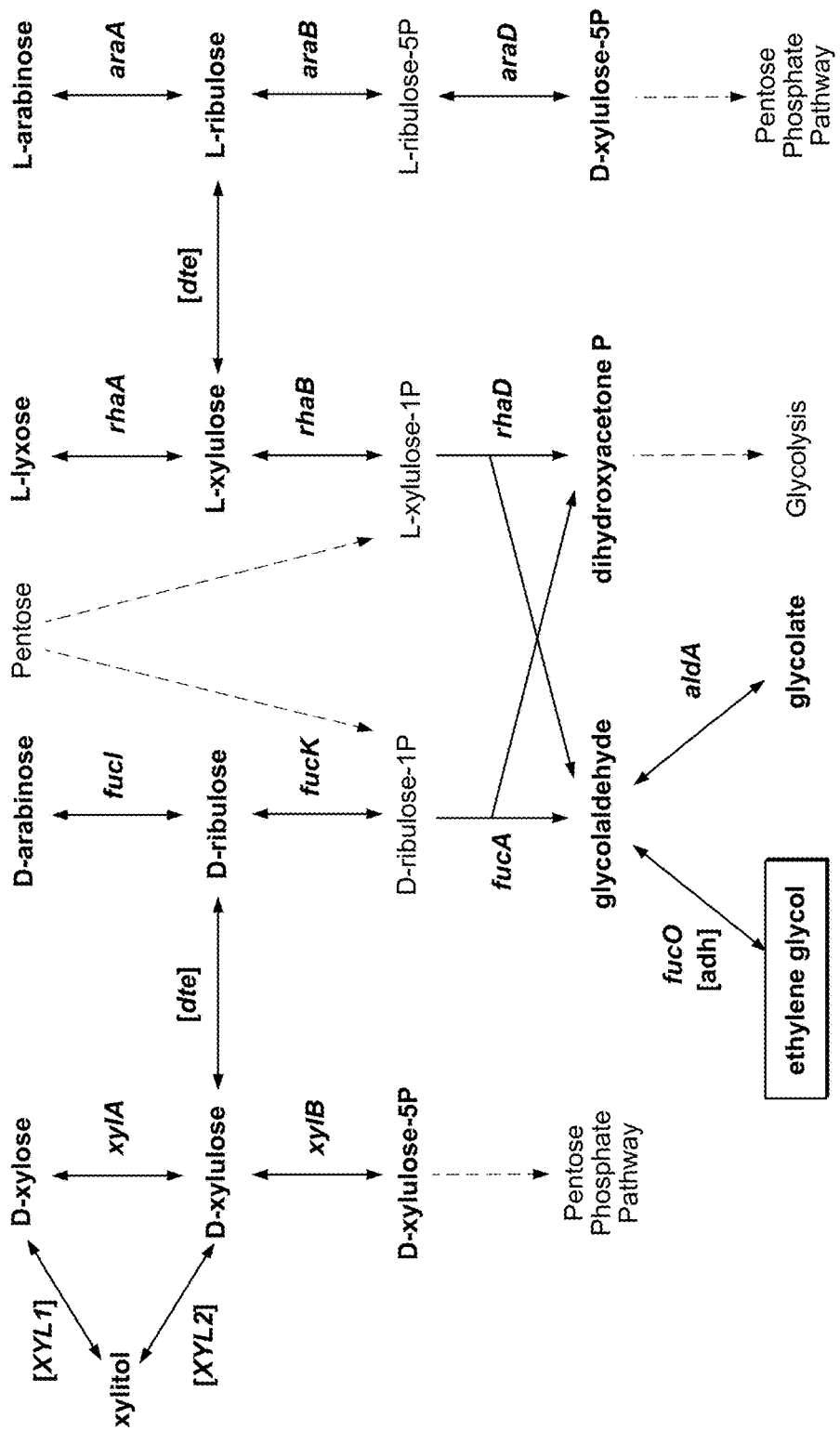
FIG. 1: Pathway map of ethylene glycol production from pentoses. Enzymes that catalyze the depicted reactions are represented by their corresponding genes (in italics); genes are from *E. coli* or from heterologous sources (within brackets).

The technology described herein is based on a pathway engineering scheme consisting of three elements: cleavage of pentoses to yield glycolaldehyde, generation of glycolaldehyde from glycolysis intermediates, and conversion of glycolaldehyde to ethylene glycol. While cleavage of the pentose will depend on the specific pentose, the latter two elements will be consistent across glycerol and all sugars.

In some embodiments, D-arabinose yields glycolaldehyde. D-arabinose can be transported into the cell through an arabinose or fucose transporter. D-arabinose isomerase converts D-arabinose to D-ribulose, and D-ribulose is phosphorylated at the 1 position by D-ribulokinase. D-ribulose-phosphate aldolase can cleave the D-ribulose-1-phosphate, thereby resulting in glycolaldehyde and dihydroxyacetone phosphate. Examples of genes encoding an arabinose transporter, D-arabinose isomerase, D-ribulokinase, and D-ribulose-phosphate aldolase are fucP, fucI, fucK, and fucA (all from *E. coli*), respectively.

In some embodiments, D-xylose yields glycolaldehyde. By means of a xylose transporter, D-xylose enters the cell where it is converted to D-xylulose. D-xylulose is formed by xylose isomerase or through the intermediate of D-xylitol by D-xylose reductase and xylitol dehydrogenase. To prevent flux toward the pentose phosphate pathway, it is important to attenuate expression or activity of xylulokinase, if present in the microbe. D-xylulose can then be converted to D-ribulose by an epimerase. As mentioned above, D-ribulose can be converted to D-ribulose-1-phosphate which is subsequently cleaved to glycolaldehyde and dihydroxyacetone phosphate. Examples of genes encoding a xylose transporter, xylose isomerase, and xylulokinase are *E. coli* genes xylE, xylA, and xylB, respectively. Furthermore, *E. coli* genes xylF, xylG, and xylH comprise another xylose transporter. Examples of genes encoding xylose reductase and xylitol dehydrogenase are *Pichia stipitis* genes XYL1 and XYL2, respectively.

In some embodiments, L-arabinose yields glycolaldehyde. L-arabinose can be taken in by the cell by a transporter and then converted to L-ribulose by L-arabinose isomerase. L-ribulose can be converted to L-xylulose by an epimerase, while a competing degradation pathway can be reduced by attenuating L-ribulokinase activity. Alternatively, L-arabinose can be converted to L-xylulose through the intermediate L-arabitol by L-arabinose reductase and L-arabitol-4-dehydrogenase. L-xylulose can then be phosphorylated by ATP:L-xylulose 1-phosphotransferase such as to yield L-xylulose-1-phosphate, which is subsequently cleaved by L-xylulose-1-phosphate aldolase to produce glycolaldehyde and dihydroxyacetone phosphate. Examples of genes encoding an L-arabinose transporter, L-arabinose isomerase, and L-ribulokinase include *E. coli* genes araE, araA and araB, respectively. *E. coli* genes araF, araG and araH comprise another L-arabinose transporter. Examples of genes encoding L-arabinose reductase and L-arabinose-4-dehydrogenase include *Aspergillus niger* genes LarA and LadA. Examples of genes encoding an ATP:L-xylulose 1-phosphotransferase and L-xylulose-1-phosphate aldolase include *E. coli* genes rhaB and rhaD, respectively.

In some embodiments that yield glycolaldehyde from L-arabinose, L-arabinose is converted to L-xylulose by one of the pathways described herein. The L-xylulose is then converted to xylitol by L-xylulose reductase, an example of which is the *Aspergillus niger* gene LxrA. Xylitol can be converted to D-xylulose, which can yield glycolaldehyde, as described herein.

In some embodiments, the epimerase which catalyzes the conversion of D-xylulose to D-ribulose and/or L-ribulose to L-xylulose is D-tagatose 3-epimerase (DTE). Sources of DTE-encoding genes (here referred to as dte) include, but are not limited to, *Pseudomonas cichorii, Rhodobacter sphaeroides, Pelagibaca bermudensis, Desmospora* sp. 8437, and *Rhizobium loti*. In some embodiments the epimerase is D-psicose 3-epimerase (DPE). Sources of DPE-encoding genes include, but are not limited to, *Agrobacterium tumefaciens* and *Clostridium cellulolyticum*. In some embodiments, the epimerase is a DTE-related protein. Such enzymes include, but are not limited to, TM0416p from *Thermotoga maritime* and, D-tagatose 3-epimerase-related protein from *Fulvimarina pelagi*. In some embodiments, the epimerase is a ribulose phosphate epimerase capable of acting on D-xylulose and/or L-ribulose.

In other embodiments, other pentoses yield glycolaldehyde. As in the cases for D-arabinose and D-xylose, a given pentose can yield glycolaldehyde if there exists a pathway to D-ribulose-1-phosphate. As in the case for L-arabinose, a given pentose can yield glycolaldehyde if there exists a pathway to L-xylulose-1-phosphate.

Figure 2:
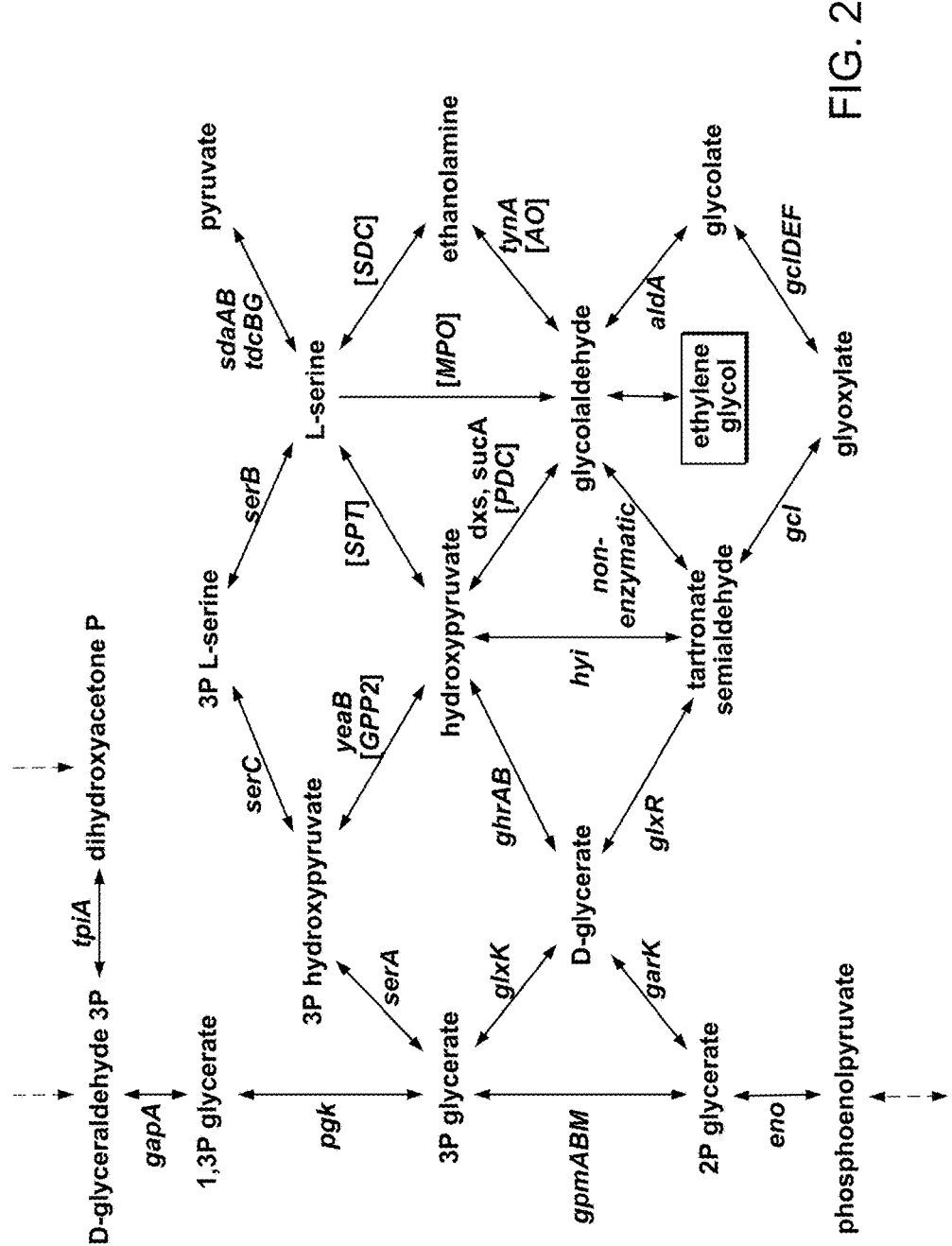
FIG. 2: Pathway map of ethylene glycol production from glycolysis intermediates. Enzymes that catalyze the depicted reactions are represented by their corresponding genes (in italics); genes are from *E. coli* or from heterologous sources (within brackets).
Figure 3:
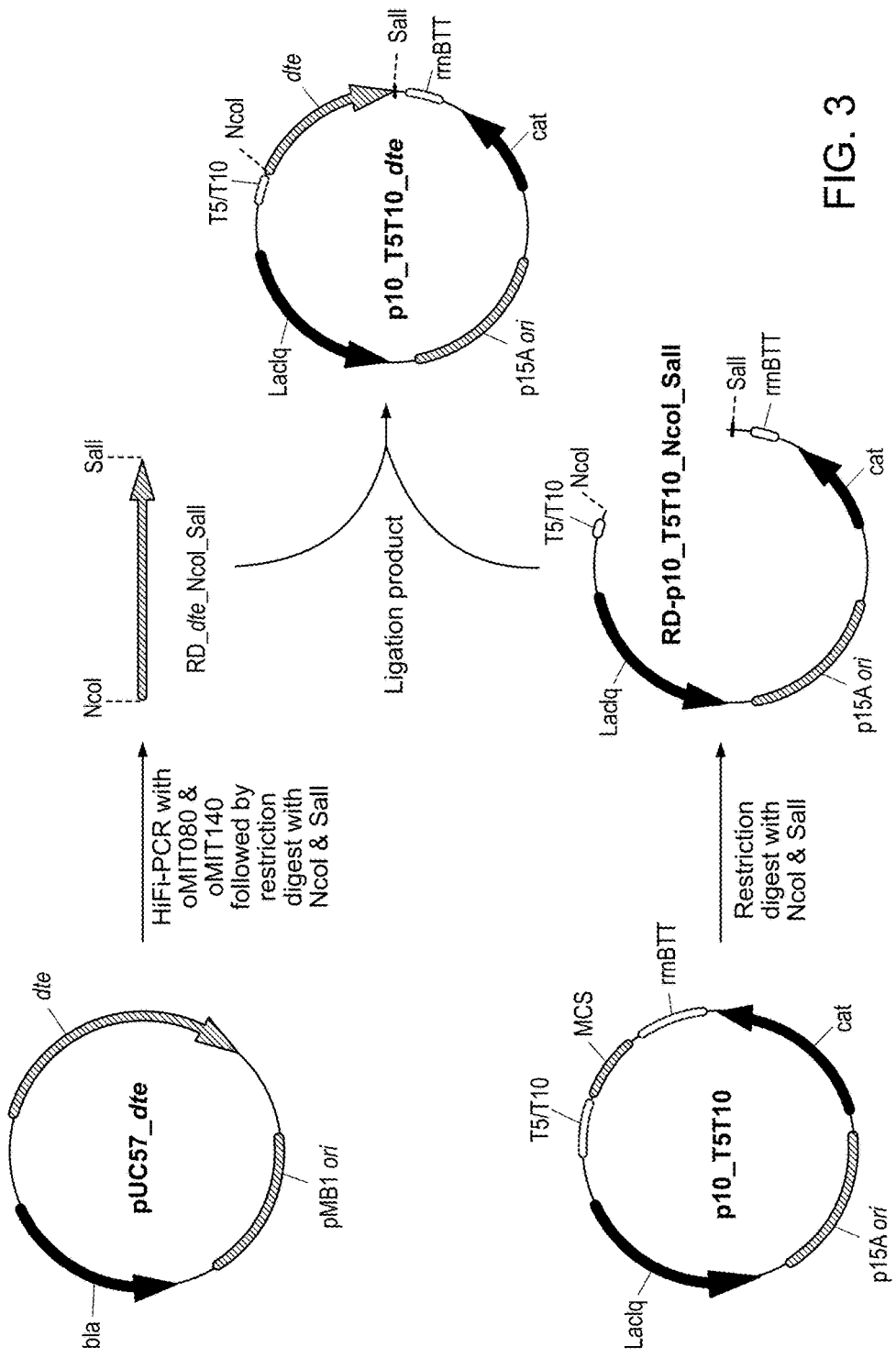
FIG. 3: Schematic overview of the construction of p10_T5T10-dte. bla=Beta-lactamase; cat=chloramphenicol acetyltransferase; dte=codon-optimized D-tagatose-3-epimerase; MCS=multi cloning site; RD=restriction digest; HiFi-PCR=High Fidelity PCR; T5T10=promoter T5T10; rrnBTT=terminator rrnBTT; oMIT080=Fw-primer 5'-GCTGCCATGGACAAAGTTGGTATGTTCTACACC (SEQ ID NO:1); 0MIT140=Rv-primer 5'AGTCGTCGACATGAGCTCCGTAGGCCGGCCTAAACGAATTCTTAGGC CAGTTTATCACGG (SEQ ID NO:2).
Figure 4A:
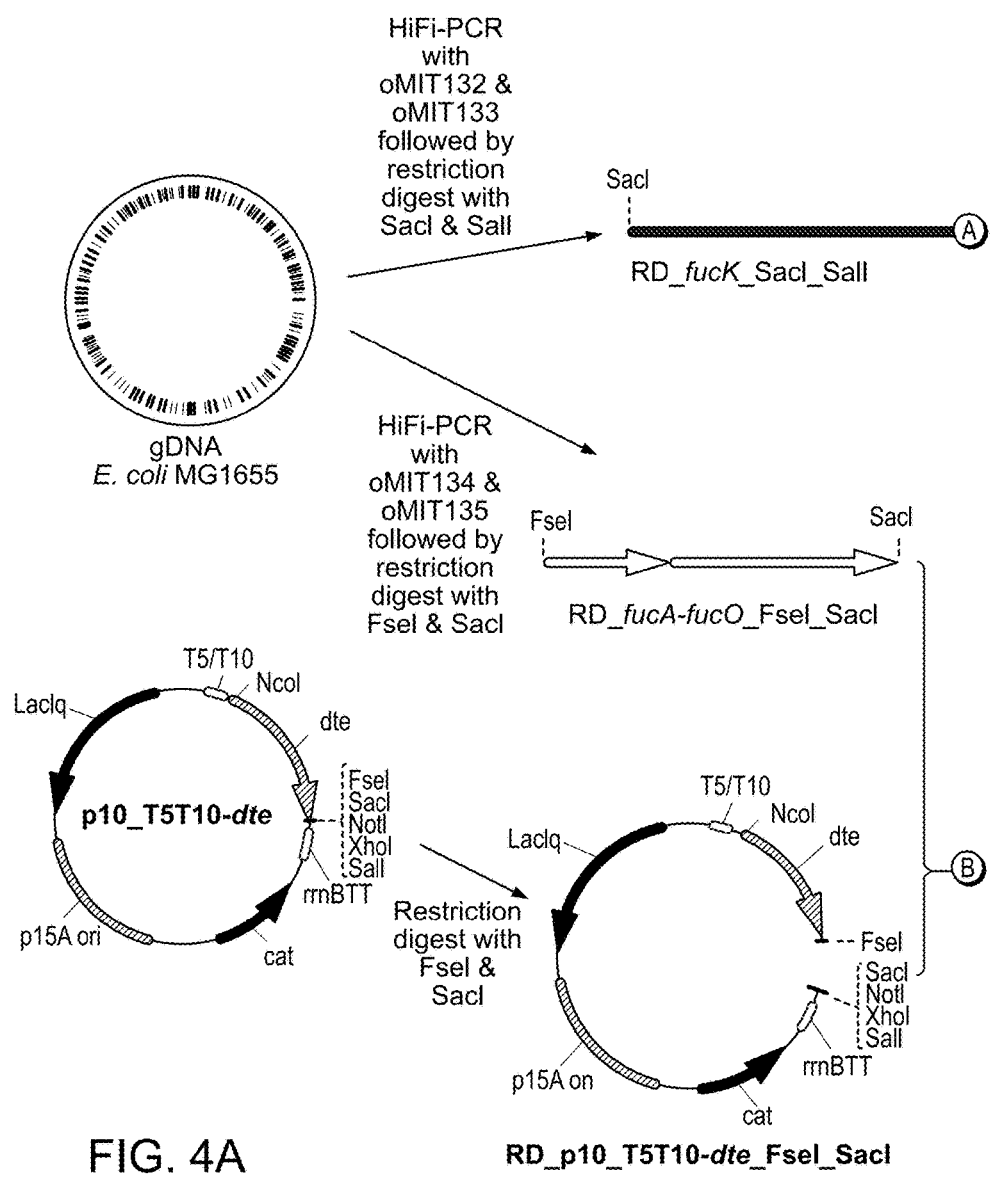
FIGS. 4A-4B: Schematic overview of the construction of p10_T5T10-dte-fucA-fucO-fucK. cat=chloramphenicol acetyltransferase; dte=codon-optimized D-tagatose-3-epimerase; gDNA=genomic DNA; MCS=multi cloning site; RD=restriction digest; HiFi-PCR=High Fidelity PCR; T5T10=promoter T5T10; rrnBTT=terminator rrnBTT; oMIT132=Fw-primer 5'-GAATTCGTTTAGAGCTCTAAATAAGGAGGAATAACCATG GTATCCGGCTATATTGCAGGAG (SEQ ID NO:3); oMIT133=Rv-primer 5'-ACTGG TCGACGCTATCTTCACACTTCCTCTATAAATTC (SEQ ID NO:4); oMIT134=Fw-primer 5'-CTGCGGCCGGC-CCTTTAATAAGGAGATATACCATGGAACGAAATAA ACTTGC (SEQ ID NO:5); oMIT135=Rv-primer 5'-GCCGGAGCTCTAAACGAATTCTT ACCAGGCGGTATGG-TAAAGC (SEQ ID NO:6).
Figure 4B:
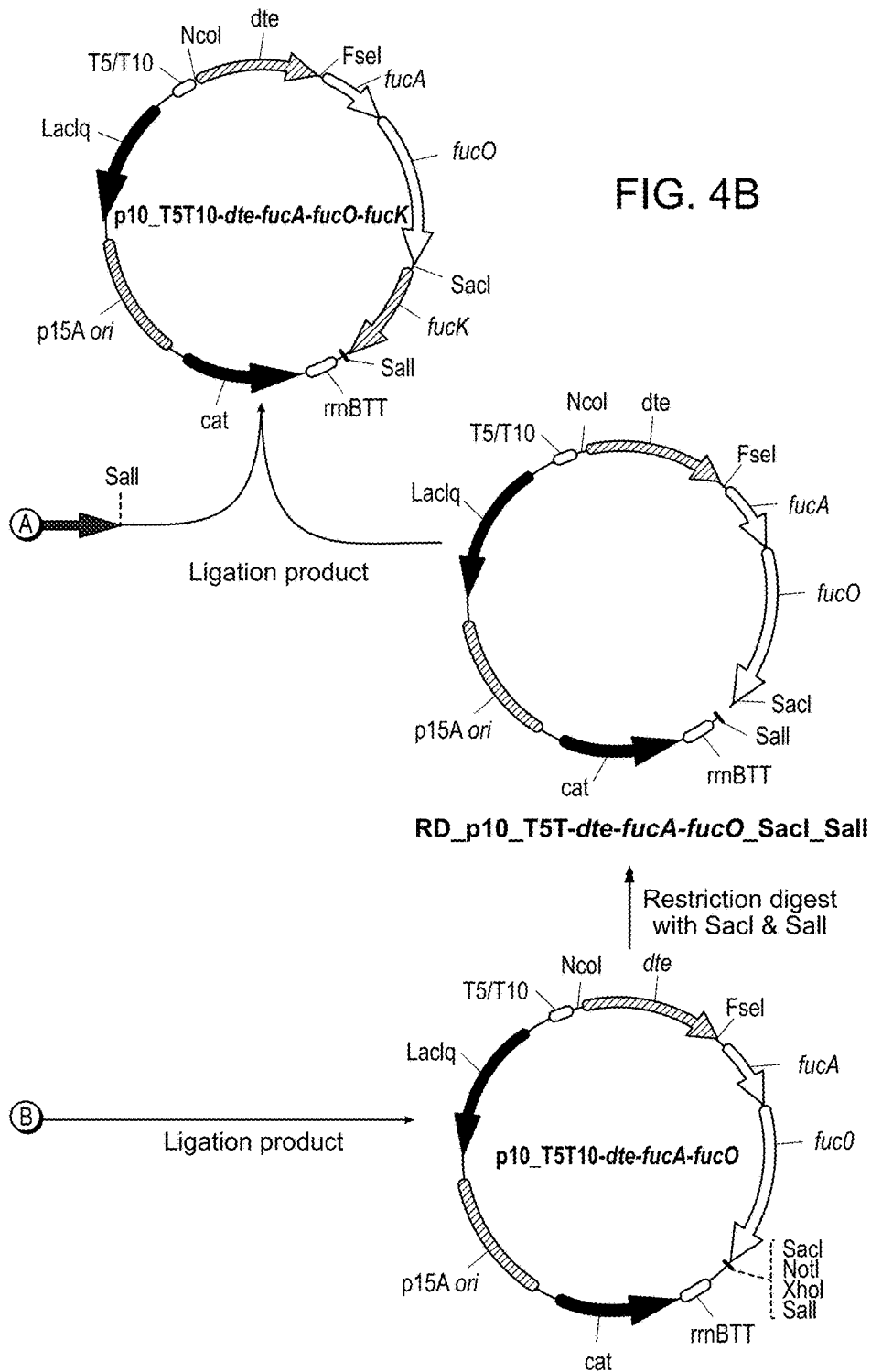
Figure 5:
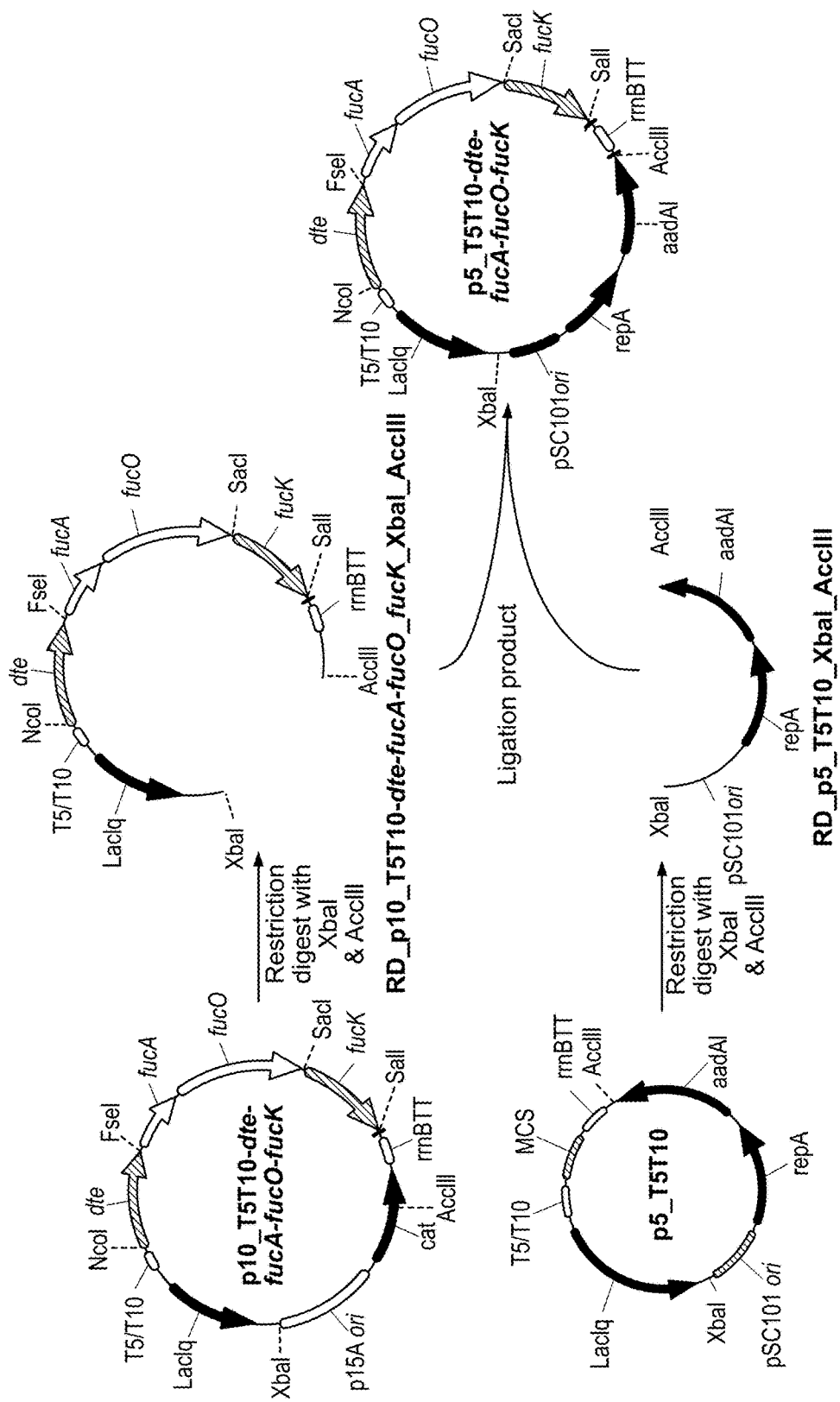
FIG. 5: Schematic overview of the construction of p5_T5T10-dte-fucA-fucO-fucK. aadA1=gentamycin resistance gene; cat=chloramphenicol acetyltransferase; dte=codon-optimized D-tagatose-3-epimerase; MCS=multi cloning site; RD=restriction digest; HiFi-PCR=High Fidelity PCR; T5T10=promoter T5T10; rrnBTT=terminator rrnBTT; repA=a plasmid-encoded gene product required for pSC101 replication in *Escherichia coli*.
Figure 6:
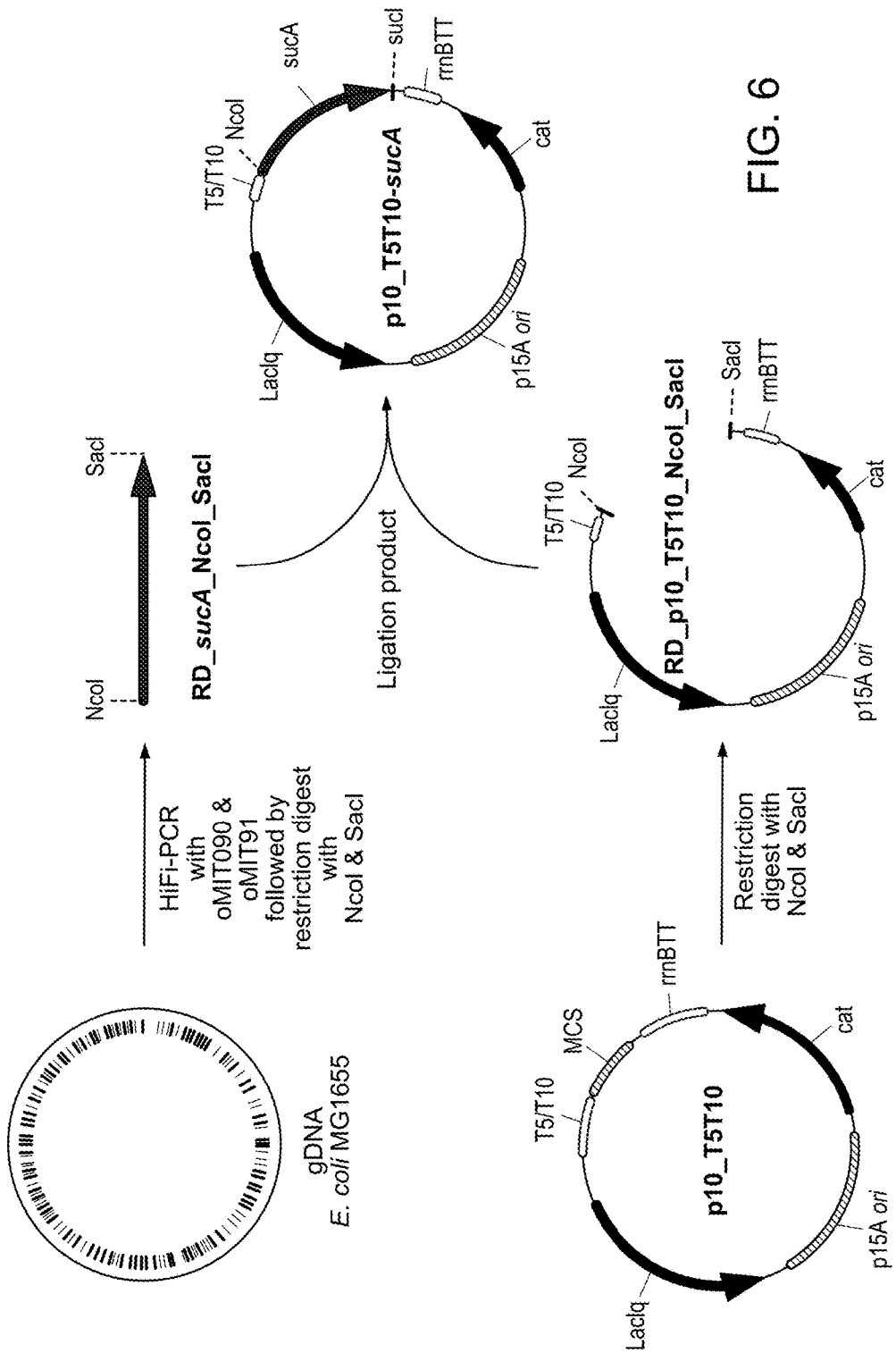
FIG. 6: Schematic overview of the construction of p10_T5T10-sucA. bla=Beta-lactamase; cat=chloramphenicol acetyltransferase; MCS=multi cloning site; RD=restriction digest; HiFi-PCR=High Fidelity PCR; T5T10=promoter T5T10; rrnBTT=terminator rrnBTT; oMIT090=Fw-primer 5'-GCTGCCATGGAGAACA-GCGCTTTGAAAGC (SEQ ID NO:7); 0MIT91=Rv-primer 5'-CTATGAGCTCCGTAGGCCGGCCTAA ACGAATTCT-TATTCGACGTTCAGCGCGTC (SEQ ID NO:8).

Glucose, glycerol, and the dihydroxyacetone phosphate resulting from cleavage of pentoses proceed through glycolysis, so another element of our pathway engineering scheme is generating glycolaldehyde from glycolysis intermediates. As shown in FIG. 2, multiple pathways are possible. In some embodiments, the pathway begins with conversion of 3-phosphoglycerate to 3-phosphohydroxypyruvate by 3-phosphoglycerate dehydrogenase. One source of 3-phosphoglycerate dehydrogenase is the serA gene from *E. coli*. In some embodiments, the pathway begins with conversion of 3-phosphoglycerate to glycerate by a glycerate kinase. An example of a glycerate kinase that may be used to convert 3-phosphoglycerate to glycerate is glycerate kinase II, which is encoded by the glxK gene in *E. coli*. In some embodiments, the pathway begins with conversion of 2-phosphoglycerate to glycerate by a glycerate kinase. An example of a glycerate kinase that may be used to convert 2-phosphoglycerate to glycerate is glycerate kinase I, which is encoded by the garK gene in *E. coli*. In some embodiments, availability of glycolysis intermediate 3-phosphoglycerate is increased by reducing flux to 2-phosphoglycerate, or availability of 2-phophoglycerate is increased by reducing flux to phosphoenolpyruvate. These fluxes can be reduced by attenuating expression or activity of phosphoglycerate mutases and of enolase, respectively. The gpmA, gpmB, and gpmM genes from *E. coli* are examples of phosphoglycerate mutase-encoding genes. The eno gene from *E. coli* is an example of an enolase-encoding gene.

In some embodiments, glycolaldehyde will be formed from tartronate semialdehyde. This reaction has been suggested to occur non-enzymatically [Hedrick 1961; Kim 2010], though there may be enzymes capable of catalyzing it.

In some embodiments, glycolaldehyde will be formed from hydroxypyruvate. This reaction has been suggested to occur non-enzymatically, though possibly through formation of tartronate semialdehyde [Hedrick 1961; Kim 2010]. Additionally, various enzymes may be used to catalyze the decarboxylation of hydroxypyruvate. The enzyme can be one specific for hydroxypyruvate, i.e., hydroxypyruvate decarboxylase; there is evidence of one such hydroxypyruvate decarboxylase in mammals [Hedrick 1964]. The enzyme can be a pyruvate decarboxylase with substrate promiscuity, capable of acting on hydroxypyruvate; an example of one such pyruvate decarboxylase is that of wheat germ [Davies 1985]. The enzyme can be a thiamine pyrophosphate-dependent enzyme with promiscuous activity, capable of decarboxylation of hydroxypyruvate. Examples of such TPP-dependent enzymes include, but are not limited to, the subunit of the E1 component of the 2-oxoglutarate dehydrogenase complex (encoded by sucA in *E. coli*) and 1-deoxyxylulose-5-phosphate synthase (encoded by dxs in *E. coli*) [Kim 2010].

In some embodiments, glycolaldehyde will be formed from L-serine. This reaction can be catalyzed by the enzyme myeloperoxidase (MPO) as part of a MPO-$H_2O_2$-chloride system [Anderson 1997]. For example, one source of myeloperoxidase is the MPO gene from *Homo sapiens*.

In some embodiments, glycolaldehyde will be formed from ethanolamine. This reaction may be catalyzed by ethanolamine oxidase or by a promiscuous amine oxidase. Evidence of an ethanolamine oxidase has been found in *Phormia regina* [Kulkarni 1973]. A promiscuous amine oxidase capable of oxidizing ethanolamine has been discovered in *Arthrobacter* sp. [Ota 2008]. In *E. coli*, tynA encodes an amine oxidase which may be capable of oxidizing ethanolamine.

In some embodiments, glycolaldehyde will be formed from glycolate. This reaction can be catalyzed by an aldehyde dehydrogenase. One example of such an aldehyde dehydrogenase is aldehyde dehydrogenase A (encoded by aldA) in *E. coli*.

Formation of 3-phosphohydroxypyruvate or D-glycerate can be combined with formation of glycolaldehyde from tartronate semialdehyde, hydroxypyruvate, L-serine, ethanolamine, or glycolate in several ways through various connecting reactions. In some embodiments 3-phosphohydroxypyruvate will be converted to 3-phospho-L-serine by 3-phosphoserine aminotransferase, and 3-phospho-L-serine will be further converted to L-serine by phosphoserine phosphatase. Examples of sources of phosphoserine aminotransferase and phosphoserine phosphatase are *E. coli* genes serC and serB, respectively. In some embodiments, conversion of L-serine to pyruvate will be reduced by attenuating serine deaminases. Examples of serine deaminases are those encoded by *E. coli* genes sdaA, sdaB, tdcB, and tdcG. In some embodiments, L-serine will be converted to ethanolamine. This reaction can be catalyzed by serine decarboxylase (SDC); SDC is found within plants including, but not limited to, *Arabidopsis thaliana* [Rontein 2001]. Some enzymes with serine decarboxylase activity may be annotated as histidine decarboxylase. Activity of SDC may possibly be increased through truncation of the N-terminal extension of the enzyme.

In some embodiments, 3-phosphohydroxypyruvate will be converted to hydroxypyruvate. This reaction can be catalyzed by an enzyme with 3-phosphohydroxypyruvate phosphatase activity. One example of such an enzyme is the predicted NUDIX hydrolase encoded by yeaB in *E. coli*; this enzyme has been shown to have 3-phosphohydroxypyruvate phosphatase activity [Kim 2010]. Another enzyme that is hypothesized to have 3-phosphohydroxypyruvate phosphatase activity, based on substrate similarity, is the glycerol-3-phosphatase encoded by GPP2 in *S. cerevisiae*. In some embodiments, L-serine will be converted to hydroxypyruvate, or hydroxypyruvate will be converted to L-serine. This reaction can be catalyzed by serine:pyruvate aminotransferase (SPT) or by alanine:glyoxylate aminotransferase (AGT). Sources of SPT and AGT include, but are not limited to, *Arabidopsis thaliana, Drosophila melanogaster, Canis lupus familiaris, Homo sapiens*, and *Rattus norvegicus*.

In some embodiments, D-glycerate will be converted to hydroxypyruvate. Examples of enzymes capable of catalyzing this reaction include, but are not limited to, glyoxylate reductases encoded by *E. coli* genes ghrA and ghrB. In some embodiments, D-glycerate will be converted to tartronate semialdehyde. Examples of enzymes capable of catalyzing this reaction include, but are not limited to, tartronate semialdehyde reductases encoded by *E. coli* genes glxR and garR. In some embodiments, hydroxypyruvate will be converted to tartronate semialdehyde, or tartronate semialdehyde to hydroxypyruvate. This reaction can be catalyzed by hydroxypyruvate isomerase. One source of hydroxypyruvate isomerase is the *E. coli* gene hyi.

In some embodiments, tartronate semialdehyde will be converted to glyoxylate. For example, one enzyme capable of catalyzing this reaction is tartronate semialdehyde synthase encoded by the *E. coli* gene gcl. In some embodiments, glyoxylate will be converted to glycolate. An example of an enzyme capable of catalyzing this reaction is glycolate oxidase encoded by *E. coli* genes glcD, glcE, and glcF.

The map presented in FIG. 2, shows the reaction space available for generating glycolaldehyde from glycolysis intermediates. Within the reaction space, there exist several pathways based on combinations of the reactions described herein.

Another aspect of this technology includes reducing glycolaldehyde to ethylene glycol. In some embodiments, this reaction is catalyzed by glycolaldehyde reductase. An example of glycolaldehyde reductase includes, but is not limited to, the enzyme encoded by the *E. coli* gene fucO. In some embodiments, glycolaldehyde conversion to ethylene glycol is catalyzed by an alcohol dehydrogenase. Examples include, but are not limited to, alcohol dehydrogenases encoded by ADH1 in *S. cerevisiae* and yqhD in *E. coli*. Some organisms can metabolize glycolaldehyde to glycolate, by an aldehyde dehydrogenase for example. In some embodiments, this reaction will be attenuated.

The pathways described herein for the production of ethylene glycol and ethylene glycol precursors in cells involve several enzymatic components. In some embodiments, the genes are expressed as part of an operon. These genes may be placed in any order in the operon. It should be appreciated that some cells compatible with the invention may express an endogenous copy of one of more of the aforementioned enzymatic components as well as a recombinant copy.

As one of ordinary skill in the art would be aware, homologous genes for these enzymes can be obtained from other species and can be identified by homology searches, for example through a protein BLAST search, available at the National Center for Biotechnology Information (NCBI) internet site (www.ncbi.nlm.nih.gov). Genes associated with the invention can be cloned, for example by PCR amplification and/or restriction digestion, from DNA from any source of DNA which contains the given gene. In some embodiments, a gene associated with the invention is synthetic. Any means of obtaining a gene encoding for an enzyme associated with the invention is compatible with the instant invention.

Aspects of the invention include strategies to optimize production of ethylene glycol from a cell. Optimized production of ethylene glycol refers to producing a higher amount of ethylene glycol following pursuit of an optimization strategy than would be achieved in the absence of such a strategy. Optimization of production of ethylene glycol can involve modifying a gene encoding for an enzyme before it is recombinantly expressed in a cell. In some embodiments, such a modification involves codon optimization for expression in a bacterial cell. For example, this includes the use of heterologous genes from various sources whose sequence has been properly modified (including codon optimization) for optimal expression in the host organism. Codon usages for a variety of organisms can be accessed in the Codon Usage Database (kazusa.or.jp/codon/). Codon optimization, including identification of optimal codons for a variety of organisms, and methods for achieving codon optimization, are familiar to one of ordinary skill in the art, and can be achieved using standard methods.

In some embodiments, modifying a gene encoding for an enzyme before it is recombinantly expressed in a cell involves making one or more mutations in the gene encoding for the enzyme before it is recombinantly expressed in a cell. For example, a mutation can involve a substitution or deletion of a single nucleotide or multiple nucleotides. In some embodiments, a mutation of one or more nucleotides in a gene encoding for an enzyme will result in a mutation in the enzyme, such as a substitution or deletion of one or more amino acids.

Additional changes can include increasing copy numbers of the gene components of pathways active in production of ethylene glycol, such as by additional episomal expression. In some embodiments, screening for mutations in components of the production of ethylene glycol, or components of other pathways, that lead to enhanced production of ethylene glycol may be conducted through a random mutagenesis screen, or through screening of known mutations. In some embodiments, shotgun cloning of genomic fragments could be used to identify genomic regions that lead to an increase in production of ethylene glycol, through screening cells or organisms that have these fragments for increased production of ethylene glycol. In some cases one or more mutations may be combined in the same cell or organism.

In some embodiments, production of ethylene glycol in a cell can be increased through manipulation of enzymes that act in the same pathway as the enzymes associated with the invention. For example, in some embodiments it may be advantageous to increase expression of an enzyme or other factor that acts upstream or downstream of a target enzyme such as an enzyme associated with the invention. This could be achieved by over-expressing the upstream or downstream factor using any standard method.

A further strategy for optimization of production of ethylene glycol is to increase expression levels of one or more genes associated with the invention, which can be described as "pathway balancing". This may be accomplished, for example, through selection of appropriate promoters and ribosome binding sites. In some embodiments, the production of ethylene glycol is increased by balancing expression of the genes such as by selecting promoters of various strengths to drive expression of the genes. In some embodiments, this may include the selection of high-copy number plasmids, or low or medium-copy number plasmids. The step of transcription termination can also be targeted for regulation of gene expression, through the introduction or elimination of structures such as stem-loops.

The invention also encompasses isolated polypeptides containing mutations or codon optimizations in residues described herein, and isolated nucleic acid molecules encoding such polypeptides. As used herein, the terms "protein" and "polypeptide" are used interchangeably and thus the term polypeptide may be used to refer to a full-length polypeptide and may also be used to refer to a fragment of a full-length polypeptide. As used herein with respect to polypeptides, proteins, or fragments thereof, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in production, nature, or in vivo systems to an extent practical and appropriate for their intended use. Substantially pure polypeptides may be obtained naturally or produced using methods described herein and may be purified with techniques well known in the art. Because an isolated protein may be admixed with other components in a preparation, the protein may comprise only a small percentage by weight of the preparation. The protein is nonetheless isolated in that it has been separated from the substances with which it may be associated in living systems, i.e. isolated from other proteins.

The invention also encompasses nucleic acids that encode for any of the polypeptides described herein, libraries that contain any of the nucleic acids and/or polypeptides described herein, and compositions that contain any of the nucleic acids and/or polypeptides described herein. It should be appreciated that libraries containing nucleic acids or proteins can be generated using methods known in the art. A library containing nucleic acids can contain fragments of genes and/or full-length genes and can contain wild-type sequences and mutated sequences. A library containing proteins can contain fragments of proteins and/or full length proteins and can contain wild-type sequences and mutated sequences. It should be appreciated that the invention encompasses codon-optimized forms of any of the nucleic acid and protein sequences described herein.

The invention encompasses any type of cell that recombinantly expresses genes associated with the invention, including prokaryotic and eukaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Preferably the yeast strain is a *S. cerevisiae* strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell, or a plant cell.

It should be appreciated that some cells compatible with the invention may express an endogenous copy of one or more of the genes associated with the invention as well as a recombinant copy. In some embodiments, if a cell has an endogenous copy of one or more of the genes associated with the invention then the methods will not necessarily require adding a recombinant copy of the gene(s) that are endogenously expressed. In some embodiments the cell may endogenously express one or more enzymes from the pathways described herein and may recombinantly express one or more other enzymes from the pathways described herein for efficient production of ethylene glycol.

In some embodiments, one or more of the genes associated with the invention is expressed in a recombinant expression vector. In other embodiments, one or more of the genes associated with the invention is expressed as or from one or more chromosomally integrated genes.

As used herein, a "vector" may be any of a number of nucleic acids into which a desired sequence or sequences may be inserted by restriction and ligation for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes of the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell. Heterologous expression of genes associated with the invention, for production of ethylene glycol, is demonstrated in the Examples using *E. coli*. The novel method for producing ethylene glycol can also be expressed in other bacterial cells, fungi (including yeast cells), plant cells, etc.

A nucleic acid molecule that encodes the enzyme of the claimed invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

In some embodiments one or more genes associated with the invention is expressed recombinantly in a bacterial cell. Bacterial cells according to the invention can be cultured in media of any type (rich or minimal) and any composition. As would be understood by one of ordinary skill in the art, routine optimization would allow for use of a variety of types of media. The selected medium can be supplemented with various additional components. Some non-limiting examples of supplemental components include one or more carbon sources such as D-arabinose, D-xylose, D-glucose, biomass hydrolysates (specifically hemicellulose) that contains D-xylose, L-arabinose, glycerol and serine; antibiotics; IPTG for gene induction; ATCC Trace Mineral Supplement; malonate; cerulenin; and glycolate. Similarly, other aspects of the medium, and growth conditions of the cells of the invention may be optimized through routine experimentation. For example, pH and temperature are non-limiting examples of factors which can be optimized. In some embodiments, factors such as choice of media, media supplements, and temperature can influence production levels of ethylene glycol. In some embodiments the concentration and amount of a supplemental component may be optimized. In some embodiments, how often the media is supplemented with one or more supplemental components, and the amount of time that the media is cultured before harvesting ethylene glycol, is optimized.

In some embodiments the temperature of the culture may be between 25 and 43° C., inclusive. For example it may be 25, 26, 27, 28, 29, 30, 31, 32, 33, 34, 35, 36, 37, 38, 39, 40, 41, 42 or 43° C., or any value in between. In certain embodiments the temperature is between 30 and 32° C. including 30, 31 and 32° C. and any value in between. In certain embodiments the temperature is between 36 and 38° C. including 36, 37 and 38° C. and any value in between. As would be understood by one of ordinary skill in the art, the optimal temperature in which to culture a cell for production of ethylene glycol may be influenced by many factors including the type of cell, the growth media and the growth conditions.

Other non-limiting factors that can be varied through routine experimentation in order to optimize production of ethylene glycol include the concentration and amount of feedstock and any supplements provided, how often the media is supplemented, and the amount of time that the media is cultured before harvesting the ethylene glycol. In some embodiments the cells may be cultured for 6, 12, 18, 24, 30, 36, 42, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, including all intermediate values, or greater than 300 hours. In some embodiments optimal production is achieved after culturing the cells for several days such as 3-4 days. However it should be appreciated that it would be routine experimentation to vary and optimize the above-mentioned parameters and other such similar parameters.

According to aspects of the invention, high titers of ethylene glycol are produced through the recombinant expression of genes associated with the invention, in a cell. As used herein "high titer" refers to a titer in the grams per liter (g/L) scale. The titer produced for a given product will be influenced by multiple factors including choice of media. In some embodiments the total ethylene glycol titer is at least 0.5 g/L (500 milligrams per liter). For example the titer may be 0.5, 0.6, 0.7, 0.8, 0.9, 1.0, 1.1, 1.2, 1.3, 1.4, 1.5, 2.0, 2.5, 3.0, 3.5, 4.0, 4.5, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, including all intermediate values, or more than 100 g/L.

The liquid cultures used to grow cells associated with the invention can be housed in any of the culture vessels known and used in the art. In some embodiments large scale production in an aerated reaction vessel such as a stirred tank reactor can be used to produce large quantities of ethylene glycol, which can be recovered from the cell culture.

EXAMPLES

The above elements have been combined into engineered strains of microbial cells. As a proof of concept, one of the engineered strains is capable of producing small amounts (25 mg/L) of ethylene glycol from D-glucose, one of the engineered strains is capable of producing small amounts of ethylene glycol from glycerol (30 mg/L), and one of the engineered strains is capable of producing 2 g/L ethylene glycol from L-arabinose. Other of the engineered strains are capable of converting greater than 30% (based on mass) of D-arabinose or D-xylose to ethylene glycol. Furthermore, with the strain engineered to use D-xylose, we have successfully produced titers of ethylene glycol greater than 40 g/L and have successfully converted hemicellulose hydrolysate (8.7 g/L xylose content) to ethylene glycol (2.7 g/L).

Thus, pathways have been constructed in engineered microbes for the production of ethylene glycol from simple sugars derived from biomass. Producing this bulk chemical biologically offers several advantages over chemical methods, and using sugars as the source material makes the ethylene glycol a "green" product. Such technology could therefore be used in the production of "green" PET products, for example "green" bottles.

Materials and Methods

Media

Luria Broth (LB) was prepared per instructions (BD, NJ, USA). M9 minimal medium consisted of M9 salts (BD, NJ, USA; 6.8 g/L $Na_2HPO_4$, 3.0 g/L $KH_2PO_4$, 0.5 g/L NaCl, and 1.0 g/L $NH_4Cl$, 2 mL/L 1M $MgSO4$, 0.1 mL/L 1M $CaCl_2$, and specified sugar. In some cases, M9 minimal medium was supplemented with 0.06 g/L Fe(III) citrate, 4.5 mg/L thiamine, and 1 mL/L trace elements solution. The trace elements solution consisted of 8.4 g/L EDTA, 2.5 g/L $CoCl_2$, 15 g/L $MnCl_2$, 1.5 g/L $CuCl_2$, 3 g/L $H_3BO_3$, 2.5 g/L $Na_2MoO_4$, and 8 g/L $Zn(CH_3COO)_2$.

M9(+) minimal medium consisted of 2.0 g/L $NH_4Cl$, 5.0 g/L $(NH_4)_2SO_4$, 3.0 g/L $KH_2PO_4$, 7.3 g/L $K_2HPO_4$, 8.4 g/L MOPS, 0.5 g/L NaCl, 2 mL/L 1M $MgSO_4$, 1 ml/l mineral solution, 0.1 mL/L 4 mM $Na_2MoO_4$, and specified sugar. The mineral solution consisted of 3.6 g/l $FeCl_2.4H_2O$, 5 g/l $CaCl_2.2H_2O$, 1.3 g/l $MnCl_2.2H_2O$, 0.38 g/l $CuCl_2.2H_2O$, 0.5 g/l CoCl$_2$.6H$_2$O, 0.94 g/l ZnCl$_2$, 0.0311 g/l H$_3$BO$_3$, 0.4 g/l Na$_2$EDTA.2H$_2$O, and 1.01 g/l thiamine-HCl. The medium was set to pH 7 with KOH.

For bioreactor fermentations, minimal medium consisted of 2.0 g/L NH$_4$Cl, 5.0 g/L (NH$_4$)$_2$SO$_4$, 2.0 g/L KH$_2$PO$_4$, 0.5 g/L NaCl, 2 mL/L 1M MgSO$_4$, 1 ml/l mineral solution, 0.1 mL/L 4 mM Na$_2$MoO$_4$, and specified sugar.

Energy cane C5 hydrolysate was pretreated by adding lime (Ca(OH)$_2$) and heating, while stirring, at 60° C. for 30 minutes; precipitation was then removed by filtration. Pretreated hydrolysate was diluted in M9(+) minimal medium to yield hydrolysate medium.

Media were sterilized by autoclaving (121° C., 21') or by filtration (0.22 μm Corning, N.Y., USA) where appropriate. When necessary, the medium was made selective by adding an antibiotic (ampicillin, chloramphenicol, kanamycin, spectinomycin). For experiments with strains harboring expression plasmids, IPTG was added to the medium.

Strains and Plasmids

*Escherichia coli* (*E. coli*) DH5α (F–, φ80dlacZΔM15, Δ(lacZYA-argF)U169, deoR, recA1, endA1, hsdR17(rk–, mk+), phoA, supE44, λ–, thi-1, gyrA96, relA1) was used to maintain plasmids. *E. coli* K-12 MG1655 ΔrecA ΔendA DE3 (provided by Professor Kristala Prather, MIT) and mutants thereof were used as production/experimental strains.

Gene disruptions (knock-out, KO) were introduced into *E. coli* using the concept of Datsenko and Wanner (2000). Transformants carrying pKD46 (Red helper plasmid, ampicillin resistance) were grown in 10 ml LB medium with ampicillin (100 mg/l) and L-arabinose (10 mM) at 30° C. to an OD$_{600}$ nm of 0.6. The cells were made electro competent by washing them with 50 ml of ice-cold water, a first time, and with 1 ml ice-cold water, a second time. Then, the cells were resuspended in 50 μl of ice-cold water. Electroporation was done with 50 μl of cells and 10-100 ng of linear double-stranded-DNA product by using a Gene Pulser® (Bio-Rad Laboratories, CA, USA) (600Ω, 25 μFD, and 250 volts). After electroporation, cells were added to 1 ml SOC medium (VWR, PA, USA) incubated 1 h at 37° C., and finally spread onto LB-agar containing 25 mg/l of chloramphenicol or 50 mg/l of kanamycin to select antibiotic resistant transformants. Mutants were verified by PCR with primers upstream and downstream of the modified region and were grown in LB-agar at 42° C. for the loss of the helper plasmid. Mutants were tested for ampicillin sensitivity. The selected mutants (chloramphenicol or kanamycin resistant) were transformed with the pCP20 plasmid, which is an ampicillin- and chloramphenicol-resistant plasmid that shows temperature-sensitive replication and thermal induction of FLP synthesis. The ampicillin-resistant transformants were selected at 30° C., after which a few were colony purified in LB at 42° C. and then tested for loss of all antibiotic resistances and of the FLP helper plasmid. The gene knock-outs were checked with control primers and sequenced.

For overexpression of enzymes, we utilized chloramphenicol-resistant p10_T5T10 and p10_T7 plasmids which were derived from the p15A plasmid, and spectinomycin-resistant p5_T5T10 and p5_T7 plasmids which were derived from the pSC101 plasmid [Ajikumar, 2010]. "T10" is another promoter region that is not active in *E. coli*. Spectinomycin-resistant pCDFDuet (Novagen, EMD Millipore, MA, USA) was also utilized. Common cloning methods using restriction enzymes and ligase enzyme were used to construct the different plasmids. The construction of several key plasmids is shown schematically in FIGS. 3-6. All plasmids were checked by PCR and/or restriction digests.

Different mutant strains were transformed with the constructed plasmids by electroporation. The cells were made electro competent and transformed as above. The selected mutants were verified by PCR using plasmid specific primers.

Cultivation Conditions

D-Arabinose Degradation Pathway

A culture, from a single colony on a LB-plate, in 3-ml LB medium was incubated overnight (o/n) at 37° C. on an orbital shaker at 200 rpm. This culture was used to inoculate to 1% v/v a 3-mL culture of M9 minimal medium with 4 g/L D-glucose; the culture was incubated o/n at 37° C., 200 rpm. This culture was used to inoculate to OD$_{600}$ 0.01 a 10-mL culture of M9 minimal medium with 4 g/L D-arabinose and 1 mM L-fucose in a 50-mL Falcon tube at 37° C., 200 rpm. Samples were taken at various time points.

Unsealed Hungate tubes with 10 mL of M9 minimal medium with 4 g/L D-arabinose, with and without 1 mM L-fucose, were placed in an anaerobic chamber (Coy Laboratory Products, MI, USA) o/n. These cultures were inoculated to OD$_{600}$ 0.01 from the aerobic D-arabinose cultures described herein, sealed with butyl rubber septa, and incubated at 37° C., 200 rpm. Samples were taken within the anaerobic chamber at various time points.

D-Arabinose and D-Xylose Comparison

A culture, from a single colony on a LB-plate, in 3-ml LB medium was incubated overnight (o/n) at 37° C. on an orbital shaker at 200 rpm. This culture was used to inoculate to 1% v/v a 3-mL culture of M9 minimal medium with 10 g/L D-glucose and supplements; the culture was incubated o/n at 37° C., 200 rpm. This culture was used to inoculate to OD$_{600}$ 0.05 a 10.8-mL culture of M9 minimal medium with supplements, 1 mM L-fucose, and either 10 g/L D-arabinose or 10 g/L D-xylose. For strains with plasmids, 1 mM IPTG and appropriate antibiotics were added to the medium. These cultures were incubated at 37° C., 200 rpm, and samples were taken at various time points.

Evaluation of Gene Order in Production from D-Xylose

A culture, from a single colony on a LB-plate, in 3-ml LB medium was incubated overnight (o/n) at 37° C. on an orbital shaker at 200 rpm. This culture was used to inoculate to 1% v/v a 3-mL culture of M9 minimal medium with 10 g/L D-glucose and supplements; the culture was incubated o/n at 37° C., 200 rpm. This culture was used to inoculate to OD$_{600}$ 0.05 a 10.8-mL culture of M9 minimal medium with supplements, and either 10 g/L D-arabinose and 1 mM L-fucose, or 10 g/L D-xylose. For strains with plasmids, 1 mM IPTG and appropriate antibiotics were added to the medium. These cultures were incubated at 37° C., 200 rpm, and samples were taken at various time points.

Production from D-Xylose in a Bioreactor

A culture, from a single colony on a LB-plate, in 3-ml LB medium was incubated overnight (o/n) at 37° C. on an orbital shaker at 200 rpm. This culture was used to inoculate to 1% v/v four 50-mL cultures of M9(+) minimal medium with 15 g/L D-glucose and spectinomycin; the cultures were incubated o/n at 37° C., 200 rpm. The cultures were combined, and 100 mL of culture was used to inoculate each bioreactor. Each bioreactor was a two-liter Bioflo® culture vessel (New Brunswick, Conn., USA) with 2.0 L minimal medium with 35 g/L D-xylose, 0.1 mM IPTG, and spectinomycin. Temperature was maintained at 37° C., and the pH was maintained at 7.0 with 6N NaOH. Aerobic conditions were maintained by sparging with air at 0.5 to 1 lpm, and dissolved oxygen content was maintained at 30% by altering agitation from 400 to 650 rpm. A solution of silicone antifoaming B emulsion (Sigma-Aldrich, MO, USA) was added when foaming occurred during the fermentation. All data was logged with the New Brunswick system (New Brunswick, Conn., USA). When nearly all D-xylose was consumed (~20 h), we initiated pumping of a feed solution into the bioreactor through a reactor port. The feed solution consisted of 600 g/L D-xylose, 10 g/L (NH$_4$)$_2$SO$_4$, 5.0 g/L MgSO$_4$, 0.1 mM IPTG, and spectinomycin. The flow rate varied from 0.05 mL/min to 0.15 mL/min. Samples were collected every four hours via a harvest pipe connected to a reactor port.

Production from Hydrolysate

A culture, from a single colony on a LB-plate, in 3-mL LB medium was incubated overnight (o/n) at 37° C. on an orbital shaker at 200 rpm. This culture was used to inoculate to 1% v/v a 10-mL culture of M9(+) minimal medium with 15 g/L D-glucose and spectinomycin; the culture was incubated o/n at 37° C., 200 rpm. The culture was used to inoculate to OD$_{600}$ 0.05 50-mL hydrolysate cultures; these consisted of pretreated hydrolysate diluted to 1/5, 2/5, 3/5, or 4/5 in M9(+) minimal medium. These cultures were incubated at 37° C., 200 rpm; samples were taken at various time points, but growth was only observed in the 1/5 dilution.

Production from L-Arabinose

A culture, from a single colony on a LB-plate or from a glycerol stock thereof, in 3-ml LB medium was incubated overnight (o/n) at 37° C. on an orbital shaker at 200 rpm. This culture was used to inoculate to 1% v/v a 3-mL culture of M9(+) minimal medium with 15 g/L D-glucose; the culture was incubated o/n at 37° C., 200 rpm. This culture was used to inoculate to OD$_{600}$ 0.05 a 50-mL culture of M9(+) minimal medium with 15 g/L L-arabinose. For strains with plasmids, 1 mM IPTG and appropriate antibiotics were added to the medium. These cultures were incubated at 37° C., 200 rpm, and samples were taken at various time points.

Production from Serine

A culture, from a single colony on a LB-plate or from a glycerol stock thereof, in 3-ml LB medium was incubated overnight (o/n) at 37° C. on an orbital shaker at 200 rpm. This culture was used to inoculate to 1% v/v a 3-mL culture of M9(+) minimal medium with 15 g/L D-glucose; the culture was incubated o/n at 37° C., 200 rpm. This culture was used to inoculate to OD$_{600}$ 0.1 a 50-mL culture of M9(+) minimal medium with 15 g/L D-glucose and 10 g/L L-serine. For strains with plasmids, 1 mM IPTG and appropriate antibiotics were added to the medium. These were incubated at 22° C., 250 rpm, and samples were taken at various time points.

Production from D-Glucose or Glycerol

A culture, from a single colony on a LB-plate, in 3-ml LB medium was incubated overnight (o/n) at 37° C. on an orbital shaker at 200 rpm. In some cases, this culture was used to inoculate to OD$_{600}$ 0.05 a 3-mL culture of M9(+) minimal medium with 15 g/L D-glucose, chloramphenicol (as necessary), and 1 mM IPTG; the culture was incubated o/n at 37° C., 200 rpm. Samples were taken after 4 days.

In other cases, the LB culture was used to inoculate to OD$_{600}$ 0.05 a 50-mL culture of M9(+) minimal medium with 1 mM IPTG and either 15 g/L D-glucose or 15.3 g/L glycerol; antibiotics were added as appropriate, and the culture was incubated o/n at 22° C., 250 rpm. Samples were taken at various time points.

Analytical Methods

Cell densities of the cultures were determined by measuring optical density at 600 nm (Ultrospec 2100 pro, Amersham (GE Healthcare), NJ, USA). The concentrations of sugars and ethylene glycol were determined in a Waters HPLC system (Waters, Mass., USA), using an Aminex HPX-87H column (Bio-Rad, CA, USA) heated at 50° C., equipped with a 1 cm precolumn, using 14 mM H$_2$SO$_4$ (0.7 ml/min) as mobile phase. A differential refractive index detector (Waters, Mass., USA) was used for analyte detection.

Example 1

Researching *E. coli* for the biological production of ethylene glycol (EG) from sugars, we noted the pathway for the degradation of D-arabinose in K-12 strains. In the pathway, the pentose intermediate D-ribulose-1-phosphate is cleaved to yield dihydroxyacetone phosphate (DHAP), which enters into glycolysis, and glycolaldehyde. Glycolaldehyde is typically oxidized to glycolate by aldehyde dehydrogenase A (encoded by the aldA gene), but as in the analogous reaction of L-lactaldehyde to L-1,2-propanediol, glycolaldehyde can also be reduced by the oxidoreductase encoded by fucO. The fluxes through these reactions depend on the availability of oxygen, so we investigated the degradation of D-arabinose under aerobic and anaerobic conditions.

Cultures of *E. coli* K-12 MG1655 DE3 ΔendA ΔrecA (referred to as wild-type or WT) and *E. coli* K-12 MG1655 DE3 ΔendA ΔrecA ΔaldA (referred to as ΔaldA) were grown aerobically and anaerobically on minimal medium with 4 g/L D-arabinose as the carbon source. After approximately nine days, we measured the concentration of ethylene glycol in the culture supernatants (Table 1). WT yielded 1.0 g/L EG when cultured anaerobically but only 0.1 g/L EG when cultured aerobically. This result confirms that *E. coli* K-12 can generate EG via the D-arabinose degradation pathway and indicates that the titer of EG is greater under anaerobic conditions. While deletion of ΔaldA only slightly improves the anaerobic production of EG relative to WT, aerobic production significantly improves. The anaerobic and aerobic titers for ΔaldA are similar, so ΔaldA can be grown aerobically without sacrificing EG production.

TABLE 1

Production of ethylene glycol from D-arabinose. *E. coli* cultures were grown on minimal medium with 4 g/L D-arabinose, and ethylene glycol concentrations were measured at 218 h (post-inoculation) for anaerobic cultures (O$_2$−) and 209 h for aerobic cultures (O$_2$+).

| Strain | O$_2$ | Ethylene Glycol (g/L) |
|---|---|---|
| WT | − | 1.0 |
| ΔaldA | − | 1.3 |
| WT | + | 0.1 |
| ΔaldA | + | 1.2 |

Example 2

Figure 7:
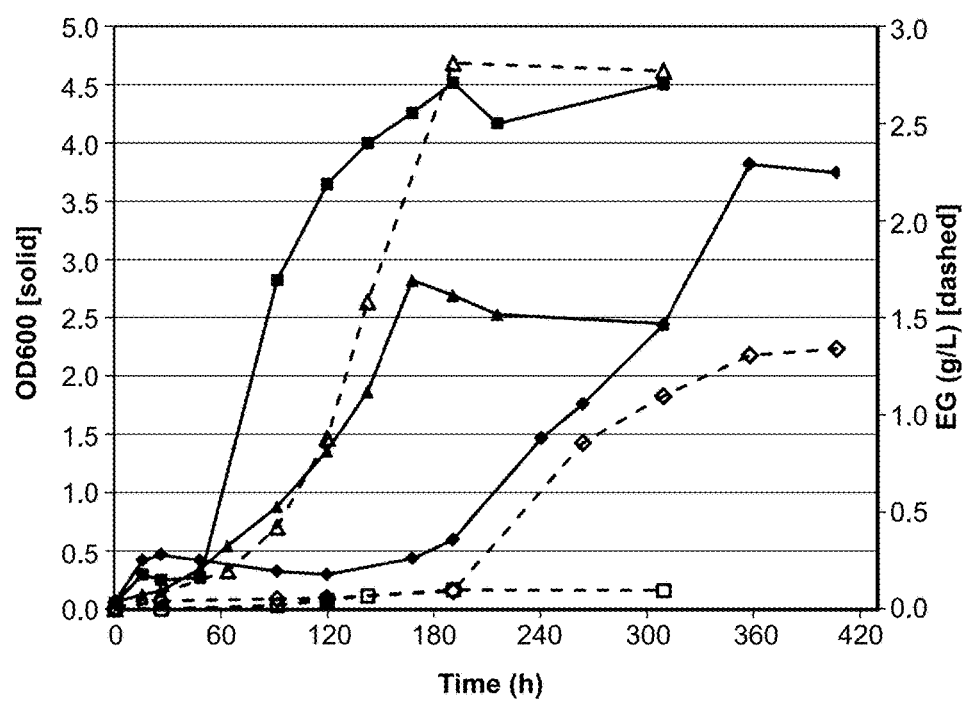
FIG. 7: Production of ethylene glycol from D-xylose. *E. coli* cultures were grown on minimal media supplemented with 10 g/L sugar, and optical densities and ethylene glycol concentrations were measured over time. Solid lines and closed symbols correspond to the optical densities ($OD_{600}$), and dashed lines and open symbols correspond to ethylene glycol concentrations in the culture supernatants. Triangles are for ΔaldA cultured on D-arabinose, squares are for ΔaldA ΔxylB cultured on D-xylose, and diamonds are for ΔaldA ΔxylB/p10_T5T10-dte cultured on D-xylose.

Though we have shown that *E. coli* is capable of generating ethylene glycol from D-arabinose, biomass-derived sugars, such as D-xylose and D-glucose, are much more abundant and therefore are preferred substrates. Because D-xylose is a pentose, we next pursued the utilization of D-xylose for EG production through the previously established D-arabinose degradation pathway. D-tagatose 3-epimerase (DTE) from *Pseudomonas cichorii* is a promiscuous enzyme that has been shown to interconvert D-xylulose and D-ribulose [Izumori 1993], intermediates of the D-xylose degradation and D-arabinose degradation pathways, respectively. Therefore, DTE (encoded by the gene here referred to as dte) can provide a path by which D-xylose can yield EG, however, conversion of D-xylulose to D-xylulose-5-phosphate, catalyzed by xylulokinase (encoded by xylB), is a competing reaction. We generated E. coli K-12 MG1655 DE3 ΔendA ΔrecA ΔaldA ΔxylB (referred to as ΔaldA ΔxylB) and transformed the strain with a plasmid overexpressing DTE (resulting in ΔaldA ΔxylB/p10_T5T10-dte). These strains were cultured with 10 g/L D-xylose and compared with ΔaldA grown on 10 g/L D-arabinose (FIG. 7).

In this experiment, we observed that ΔaldA ΔxylB is still capable of growing on D-xylose (FIG. 3, squares), even though ΔaldA ΔxylB lacks xylulokinase. The ΔaldA ΔxylB strain grows more slowly than WT (data not shown), and the pathway by which D-xylose is metabolized does not lead to any significant EG production. Overexpressing DTE in ΔaldA ΔxylB provides the connection between D-xylulose and D-ribulose and consequently leads to EG production (FIG. 7, diamonds). Though this strain successfully shows the ability to produce EG, compared to ΔaldA grown on D-arabinose (FIG. 7, triangles), the final titer is reduced and growth takes much longer. An improved strain should be able to at least match the D-arabinose results.

Example 3

Figure 8:
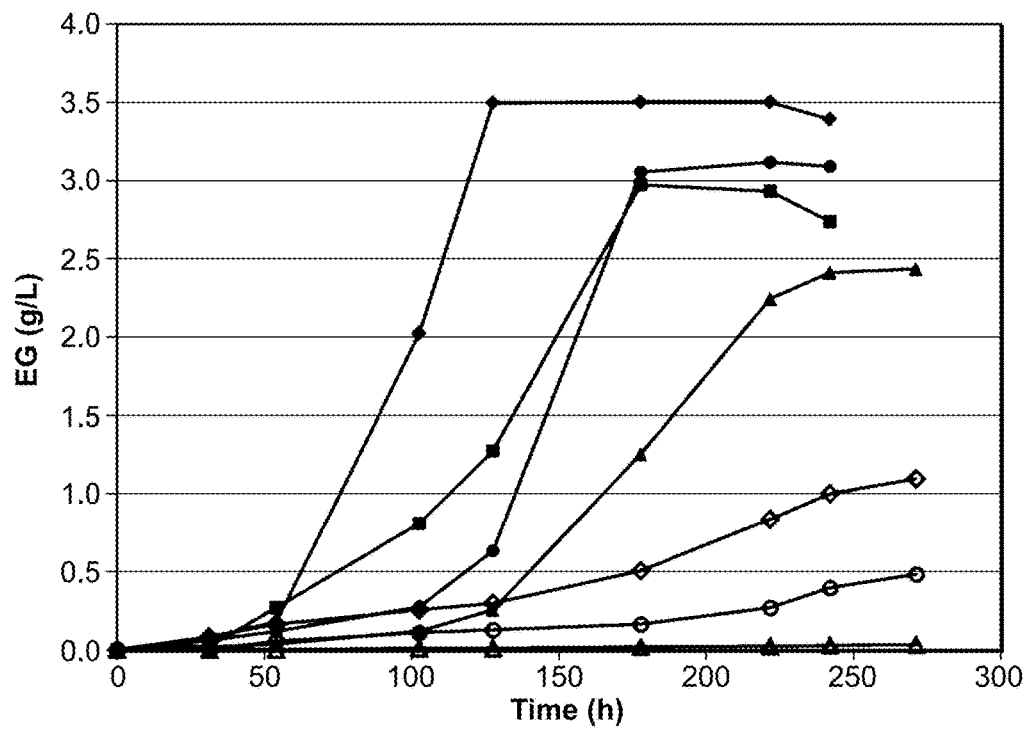
FIG. 8: Effect of gene order on production of ethylene glycol from D-xylose. *E. coli* cultures were grown on minimal media supplemented with 10 g/L xylose except for ΔaldA ΔxylB which was grown on D-arabinose. Ethylene glycol concentrations in the culture supernatants were measured over time. Closed squares are ΔaldA ΔxylB; closed diamonds are ΔaldA ΔxylB/p10_T5T10-dte-fucA-fucO-fucK; open triangles are ΔaldA ΔxylB/p10_T5T10-dte-fucK-fucA-fucO; open circles are ΔaldA ΔxylB/p10_T5T10-fucA-fucO-dte-fucK; open diamonds are ΔaldA ΔxylB/p10_T5T10-fucA-fucO-fucK-dte; closed triangles are ΔaldA ΔxylB/p10_T5T10-fucK-dte-fucA-fucO; closed circles are ΔaldA ΔxylB/p10_T5T10-fucK-fucA-fucO-dte.

To improve metabolism of D-xylose through the D-arabinose degradation pathway, we attempted to overexpress the relevant enzymes: D-ribulokinase (encoded by fucK), D-ribulose-phosphate aldolase (encoded by fucA), and glycolaldehyde reductase (encoded by fucO). These enzymes were overexpressed as part of an operon in conjunction with DTE; the order of the genes in the operon was varied. All of these were grown on D-xylose, analyzed for EG production, and compared against ΔaldA cultured on D-arabinose (FIG. 8). The best strain is ΔaldA ΔxylB/p10_T5T10-dte-fucA-fucO-fucK, which outperforms the D-arabinose results. When a plasmid of a lower copy number was used (p5_T5T10-dte-fucA-fucO-fucK), the results were similar (data not shown).

Figure 9:
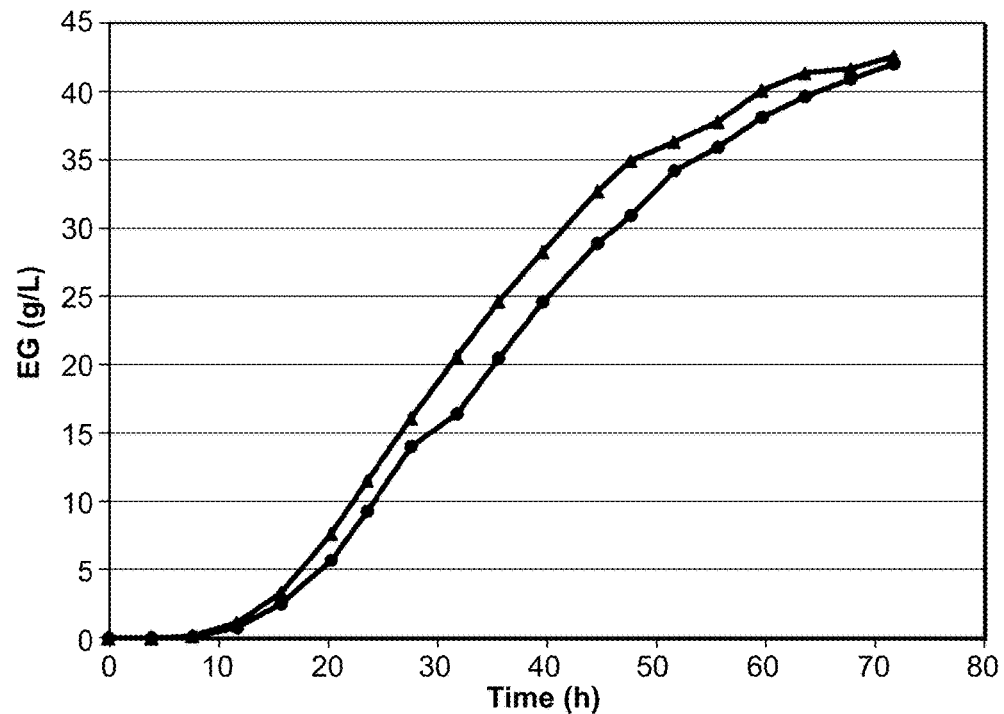
FIG. 9: Production of EG from D-xylose within a bioreactor. ΔaldA ΔxylB/p10_T5T10-dte-fucA-fucO-fucK was grown in a bioreactor in minimal medium supplemented with D-xylose. The bioreactor was run as fed-batch. EG concentrations of duplicate bioreactors are shown.

To maximize EG production, we next grew our best strain, ΔaldA ΔxylB/p5_T5T10-dte-fucA-fucO-fucK, in a bioreactor. The medium of the initial batch was minimal medium with 30 g/L D-xylose; when nearly all D-xylose was consumed, additional D-xylose was fed into the bioreactor. Ethylene glycol concentrations were measured over time (FIG. 9). Our engineered E. coli produced 42 g/L EG from D-xylose over a 72-h time frame.

Though the strain is capable of utilizing pure D-xylose as the substrate, the abundance of D-xylose is based on its presence in biomass, specifically hemicellulose. D-xylose is made available by hydrolyzing the hemicellulose, so we tested the ability of our engineered E. coli to produce EG from such hydrolysate. We prepared a medium in which pretreated hydrolysate was diluted to 1/5 and supplemented with minimal medium; the substrate was ~8.7 g/L D-xylose contributed by the hydrolysate. ΔaldA ΔxylB/p10_T5T10-dte-fucA-fucO-fucK was grown in this medium, and we measured the final EG concentration from the supernatant. The strain yielded 2.7 g/L EG.

Example 4

In the engineered strains of Examples 1-3, production of EG from a pentose (D-xylose or D-arabinose) proceeds through the intermediate D-ribulose-1-phosphate. Any pentose that can be converted to D-ribulose-1-phosphate can subsequently be used to produce EG, however, for production of EG from a pentose, it is not necessary to convert the pentose to D-ribulose-1-phosphate. In this example, we show that production of EG from a pentose can proceed through an alternative pathway.

As described earlier and as shown in FIG. 1, the pentose L-lyxose can be converted to L-xylulose-1-phosphate which can be cleaved by L-xylulose-1-phosphate aldolase. The cleavage yields dihydroxyacetone phosphate and glycolaldehyde which is subsequently converted to ethylene glycol. Furthermore, E. coli is capable of degrading the pentose L-arabinose through the intermediate L-ribulose (FIG. 1). We thus hypothesized that L-arabinose could yield glycolaldehyde, and therefore, ethylene glycol: L-arabinose would be converted to L-ribulose which could be converted to L-xylulose by DTE; L-xylulose would be phosphorylated to L-xylulose-1-phosphate which would be cleaved by its respective aldolase.

Figure 10:
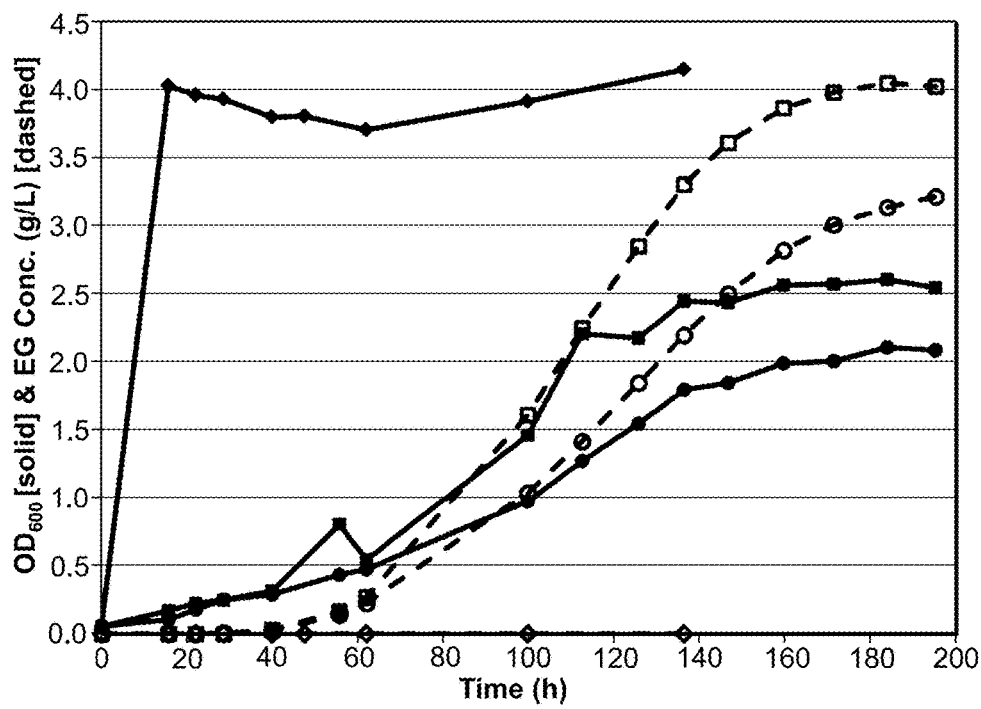
FIG. 10: Production of EG from L-arabinose. *E. coli* cultures were grown on minimal medium supplemented with 15 g/L L-arabinose. $OD_{600}$ (solid lines and closed symbols) and ethylene glycol concentrations in the culture supernatants (dashed lines and open symbols) were measured over time. Diamonds represent ΔaldA, while squares and circles represent duplicate cultures of ΔaldA ΔaraB/p10_T7-dte-rhaB-rhaD-fucO.

To validate the hypothesis, we first attenuated the native L-arabinose degradation pathway from E. coli by knocking out the gene coding for L-ribulokinase, araB. This was done in our ΔaldA strain, yielding E. coli K-12 MG1655 DE3 ΔendA ΔrecA ΔaldA ΔaraB (referred to as ΔaldA ΔaraB). We next constructed a plasmid to overexpress DTE, the enzymes for L-lyxose degradation, and glycolaldehyde reductase: p10_T7-dte-rhaB-rhaD-fucO. After transforming p10_T7-dte-rhaB-rhaD-fucO into ΔaldA ΔaraB, we cultured the strain in M9(+) with L-arabinose. As seen in FIG. 10, our engineered strain ΔaldA ΔaraB/p10_T7-dte-rhaB-rhaD-fucO produced greater than 2.0 g/L ethylene glycol from L-arabinose; the control ΔaldA grew but did not produce ethylene glycol. This experiment confirmed that ethylene glycol can be produced from L-arabinose and that pentoses can yield ethylene glycolaldehyde through the intermediate L-xylulose-1-phosphate.

Example 5

In the above work with D-arabinose, D-xylose, and L-arabinose, the pentose is cleaved into a two-carbon molecule and a three-carbon molecule; all of the EG reported has been generated from the two-carbon molecule resulting from this cleavage. The three-carbon molecule is dihydroxyacetone phosphate, which enters into glycolysis. D-glucose is also metabolized through glycolysis, so that full utilization of D-xylose and utilization of D-glucose for EG production require an additional pathway by which a glycolysis intermediate can be converted to EG. There are multiple possible pathways stemming from either 3-phosphoglycerate or 2-phosphoglycerate. To increase availability of 3-phosphoglycerate, we knocked out phosphoglycerate mutases from the ΔaldA ΔxylB strain, generating E. coli K-12 MG1655 DE3 ΔendA ΔrecA ΔaldA ΔxylB ΔgpmA (referred to as ΔaldA ΔxylB ΔgpmA), E. coli K-12 MG1655 DE3 ΔendA ΔrecA ΔaldA ΔxylB ΔgpmB (referred to as ΔaldA ΔxylB ΔgpmB), and E. coli K-12 MG1655 DE3 ΔendA ΔrecA ΔaldA ΔxylB ΔgpmA ΔgpmB (referred to as ΔaldA ΔxylB ΔgpmA ΔgpmB). These strains were cultured on minimal medium with 15 g/L D-glucose, but no ethylene glycol was detected (Table 2).

One pathway from 3-phosphoglycerate to ethylene glycol proceeds through 3-phosphohydroxypyruvate to hydroxypyruvate to glycolaldehyde and then to ethylene glycol. The conversion of 3-phosphoglycerate to 3-phosphohydroxypyruvate can be catalyzed by 3-phosphoglycerate dehydrogenase, and conversion of 3-phosphohydroxypyruvate to hydroxypyruvate requires 3-phosphohydroxypyruvate phosphatase activity. On this basis we generated plasmids containing combinations of E. coli genes serA and yeaB. These plasmids were transformed into ΔaldA ΔxylB, and the strains were cultured on minimal medium with 15 g/L D-glucose. Ethylene glycol was not detected for these strains (Table 2).

Once hydroxypyruvate is formed, it undergoes a decarboxylation to form glycolaldehyde. The decarboxylation can be carried out by an enzyme that acts specifically to decarboxylate hydroxypyruvate or a decarboxylase that primarily acts on another substrate but may also be capable of decarboxylating hydroxypyruvate. To test such enzymes, we overexpressed pyruvate decarboxylase (encoded by pdc, S. cerevisiae's PDC1 gene codon-optimized for E. coli), the subunit of the E1 component of 2-oxoglutarate dehydrogenase (encoded by sucA from E. coli), and 1-deoxyxylulose-5-phosphate synthase (encoded by dxs from E. coli). These enzymes were overexpressed within ΔaldA ΔxylB; sucA was also overexpressed within ΔaldA ΔxylB ΔgpmA and ΔaldA ΔxylB ΔgpmB. These strains were cultured on minimal medium with 15 g/L D-glucose. We were able to detect 2 mg/L ethylene glycol from ΔaldA ΔxylB/p10_T5T10-pdc and 30 mg/L from ΔaldA ΔxylB/p10_T5T10-sucA (Table 2); these results confirm that it is possible to biologically produce ethylene glycol from D-glucose.

After hydroxypyruvate is decarboxylated to glycolaldehyde, glycolaldehyde is converted to ethylene glycol by glycolaldehyde reductase or alcohol dehydrogenase. We generated plasmids with E. coli fucO, alone and in combination with sucA. These plasmids were transformed into ΔaldA ΔxylB, and the strains were cultured on minimal medium with 15 g/L D-glucose. Ethylene glycol was not detected for ΔaldA ΔxylB/p10_T5T10-fucO, but ΔaldA ΔxylB/p10_T5T10-sucA-fucO yielded 29 mg/L ethylene glycol (Table 2).

TABLE 2

Production of ethylene glycol from D-glucose through hydroxypyruvate. E. coli cultures were grown on minimal medium with 15 g/L D-glucose, and ethylene glycol concentrations were measured after 4 days (post-inoculation).

| Strain | Ethylene Glycol (mg/L) |
|---|---|
| ΔaldA ΔxylB | ND |
| ΔaldA ΔxylB ΔgpmA | ND |
| ΔaldA ΔxylB ΔgpmB | ND |
| ΔaldA ΔxylB ΔgpmA ΔgpmB | ND |
| ΔaldA ΔxylB/p10_T5T10-serA | ND |
| ΔaldA ΔxylB/p10_T5T10-serA-yeaB | ND |
| ΔaldA Δxy/B/p10_T5T10-yeaB | ND |
| ΔaldA ΔxylB/p10_T5T10-yeaB-serA | ND |
| ΔaldA ΔxylB/p10_T5T10-dxs | ND |
| ΔaldA ΔxylB/p10_T5T10-pdc | 2 |
| ΔaldA ΔxylB/p10_T5T10-sucA | 30 |
| ΔaldA ΔxylB ΔgpmA/p10_T5T10-sucA | 12 |
| ΔaldA ΔxylB ΔgpmB/p10_T5T10-sucA | 29 |
| ΔaldA ΔxylB/p10_T5T10-fucO | ND |
| ΔaldA ΔxylB/p10_T5T10-sucA-/fucO | 29 |

ND = Not Detected.

Example 6

Figure 11:
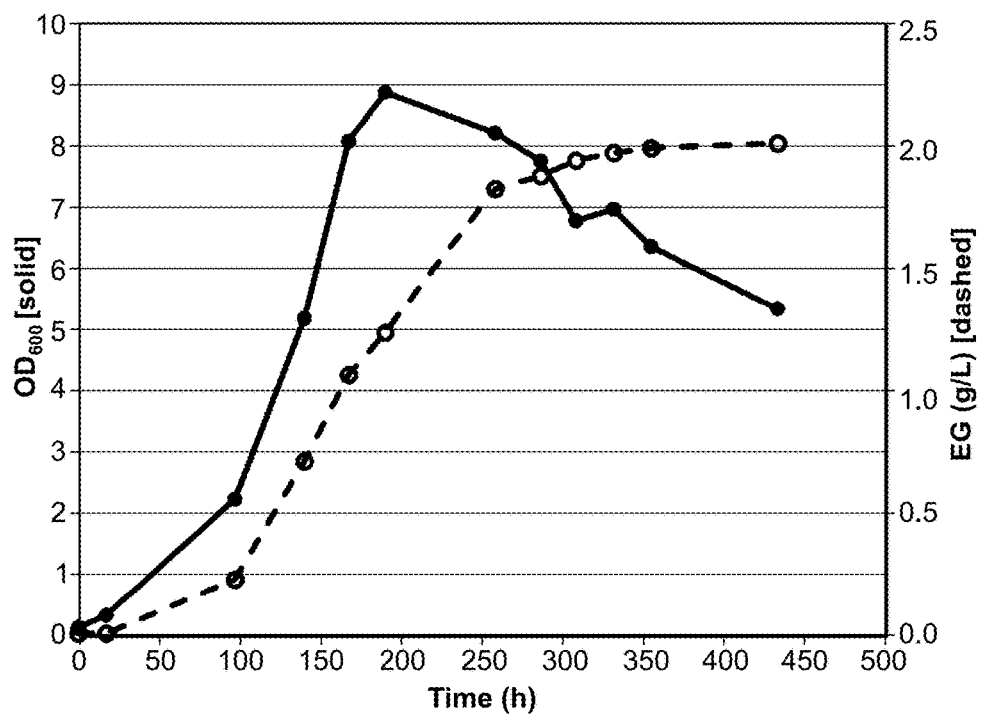
FIG. 11: Production of EG from serine. A culture of *E. coli* strain ΔaldA/pCDFDuet_T7-t-sdc+T7-aao/p10_T7-fucO were grown on minimal medium supplemented with 15 g/L D-glucose and 10 g/L L-serine. $OD_{600}$ (solid lines and closed symbols) and ethylene glycol concentrations in the culture supernatant (dashed lines and open symbols) were measured over time.

Another possible pathway to generate glycolaldehyde from the glycolysis intermediate 3-phosphoglycerate is through serine biosynthesis followed by serine decarboxylation and then ethanolamine oxidation. We investigated this pathway by testing whether an engineered microbe can produce ethylene glycol from serine. The Arabidopsis thaliana serine decarboxylase gene (sdc) [Rontein 2001] and the amine oxidase with ethanolamine oxidase activity from Arthrobacter sp. (aao) [Ota 2008] were codon-optimized for E. coli. A truncated version of sdc, starting at Met58 (hereby referred to as t-sdc), and aao were cloned into a plasmid for overexpression: pCDFDuet_T7-t-sdc+T7-aao. E. coli fucO was cloned into a separate plasmid for overexpression: p10_T7-fucO. These plasmids were transformed into the ΔaldA strain, and the resulting strain was cultured in minimal medium with glucose and serine. As demonstrated by FIG. 11, the strain ΔaLdA/pCDFDuet_T7-t-sdc+T7-aao/p10_T7-fucO was able to produce approximately 2 g/L ethylene glycol from serine.

Example 7

After strain ΔaLdA/pCDFDuet_T7-t-sdc+T7-aao/p10_T7-fucO was confirmed to produce ethylene glycol from serine, it was tested for production of ethylene glycol from D-glucose or glycerol. The strain was cultured independently on minimal medium with glucose and minimal medium with glycerol.

TABLE 3

Production of ethylene glycol from D-glucose and glycerol through ethanolamine. Cultures of E. coli strain ΔaldA/pCDFDuet_T7-t-sdc + T7-aao/p10_T7-fucO were grown on minimal medium with 15 g/L D-glucose or minimal medium with 15.3 g/L glycerol, and ethylene glycol concentrations were measured after 10 days (post-inoculation).

| Substrate | Ethylene Glycol (mg/L) |
|---|---|
| D-Glucose | 15 |
| Glycerol | 35 |

The results presented here show that our engineered microbes can generate ethylene glycol from D-arabinose, D-xylose, hemicellulose hydrolysate, L-arabinose, serine, D-glucose, and glycerol.

REFERENCES

Ajikumar, P. K., Xiao, W. H., Tyo, K. E. J., Wang, Y., Simeon, F., Leonard, E., Mucha, O., Phon, T. H., Pfeifer, B., and Stephanopoulos, G. (2010). Isoprenoid pathway optimization for taxol precursor overproduction in Escherichia coli. Science, 330 (6000), 70-74.

Anderson, M. M., Hazen, S. L., Hsu, F. F. & Heinecke, J. W. (1997). Human neutrophils employ the myeloperoxidase-hydrogen peroxide-chloride system to convert hydroxylamino acids into glycolaldehyde, 2-hydroxypropanal, and acrolein: A mechanism for the generation of highly reactive α-hydroxy and α,β-unsaturated aldehydes by phagocytes at sites of inflammation. Journal of Clinical Investigation, 99 (3), 424-432.

Chiu, T. H., Evans, K. L., & Feingold, D. S. (1975). L-Rhamnulose-1-phosphate aldolase. Methods in Enzymology, 42, 264-269.

Davies, D. D. & Asker, H. (1985). The enzymatic decarboxylation of hydroxypyruvate associated with purified pyruvate decarboxylase from wheat germ. Phytochemistry, 24 (2), 231-234.

Hedrick, J. L. & Sallach, H. J. (1961). The metabolism of hydroxypyruvate: I. The nonenzymatic decarboxylation and autoxidation of hydroxypyruvate. The Journal of Biological Chemistry, 236 (7), 1867-1871.

Hedrick, J. L. & Sallach, H. J. (1964). The nonoxidative decarboxylation of hydroxypyruvate in mammalian systems. *Archives of Biochemistry and Biophysics*, 105 (2), 261-269.

Izumori, K., Khan, A. R., Okaya, H. & Tsumura, T. (1993). A new enzyme, D-ketohexose 3-epimerase, from *Pseudomonas* sp. ST-24. *Bioscience Biotechnology and Biochemistry*, 57 (6), 1037-1039.

Kulkarni, A. P. & Hodgson, E. (1973). Ethanolamine oxidase from the blowfly *Phormia regina* (diptera: insecta). *Comparative Biochemistry and Physiology*, 44 (2B), 407-422.

Ota, H., Tamezane, H., Sasano, Y., Hokazono, E., Yasuda, Y., Sakasegawa, S., Imamura, S., Tamura, T. & Osawa, S. (2008). Enzymatic characterization of an amine oxidase from *Arthrobacter* sp. used to measure phosphatidylethanolamine. *Bioscience Biotechnology and Biochemistry*, 72 (10), 2732-2738.

Rontein, D., Nishida, I., Tashiro, G., Yoshioka, K., Wu, W. I., Voelker, D. R., Basset, G. & Hanson, A. D. (2001). Plants synthesize ethanolamine by direct decarboxylation of serine using a pyridoxal phosphate enzyme. *Journal of Biological Chemistry*, 276 (38), 35523-35529.

EQUIVALENTS

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. Such equivalents are intended to be encompassed by the following claims. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

All references, patents and patent applications disclosed herein are incorporated by reference with respect to the subject matter for which each is cited, which in some cases may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A bacterial cell engineered to produce glycolaldehyde from xylose, wherein the cell has reduced or eliminated activity of, or reduced or eliminated expression of, xylulokinase relative to a wild-type cell, the cell has reduced or eliminated activity or reduced or eliminated expression of aldehyde dehydrogenase A relative to a wild-type cell, and the cell recombinantly expresses an enzyme that interconverts xylulose and ribulose.

2. The cell of claim 1, wherein the enzyme that interconverts xylulose and ribulose is D-tagatose 3-epimerase.

3. The cell of claim 2, wherein the D-tagatose 3-epimerase is encoded by a dte gene obtained from *Pseudomonas cichorii*.

4. The cell of claim 1, wherein the cell further recombinantly expresses D-ribulokinase.

5. The cell of claim 4, wherein the D-ribulokinase is encoded by a fucK gene obtained from *Escherichia coli*.

6. The cell of claim 4, wherein the cell further recombinantly expresses D-ribulose-phosphate aldolase.

7. The cell of claim 6, wherein the cell further has reduced or eliminated activity or reduced or eliminated expression of L-ribulokinase relative to a wild-type cell.

8. The cell of claim 7, wherein the cell further recombinantly expresses ATP:L-xylulose 1-phosphotransferase, L-xylulose-1-phosphate aldolase and a glycolaldehyde reductase.

9. The cell of claim 1, wherein the cell is an *Escherichia coli* cell.

10. The cell of claim 6, wherein the D-ribulose-phosphate aldolase is encoded by a fucA gene obtained from *Escherichia coli*.

11. The cell of claim 6, wherein the cell is an *Escherichia coli* cell and the xylulokinase is encoded by a xylB gene.

12. The cell of claim 6, wherein the cell further recombinantly expresses a glycolaldehyde reductase.

13. The cell of claim 12, wherein the glycolaldehyde reductase is encoded by a fucO gene obtained from *Escherichia coli*.

14. The cell of claim 1, wherein the cell comprises a deletion of a gene encoding aldehyde dehydrogenase A and/or a deletion of a gene encoding xylulokinase.

15. The cell of claim 14, wherein the cell is an *Escherichia coli* cell and the aldehyde dehydrogenase A is encoded by an aldA gene and/or the xylulokinase is encoded by a xylB gene.

16. A method of producing ethylene glycol, comprising culturing the cell of claim 1 in the presence of xylose under conditions that result in the production of ethylene glycol.

17. A method of producing glycolaldehyde, comprising culturing the cell of claim 6 in the presence of xylose under conditions that result in the production of glycoaldehyde.

18. An *Escherichia coli* cell engineered to produce glycolaldehyde, wherein the cell comprises a deletion of a xylB gene and recombinantly expresses a dte gene obtained from *Pseudomonas cichorii*, a fucK gene obtained from *Escherichia coli*, and a fucA gene obtained from *Escherichia coli*.

19. A method of producing glycolaldehyde, comprising culturing the cell of claim 18 in the presence of xylose under conditions that result in the production of glycoaldehyde.

20. An *Escherichia coli* cell engineered to produce ethylene glycol, wherein the cell comprises a deletion of a xylB gene and an aldA gene, and recombinantly expresses a dte gene obtained from *Pseudomonas cichorii*, a fucK gene obtained from *Escherichia coli*, a fucA gene obtained from *Escherichia coli*, and a fucO gene obtained from *Escherichia coli*.

21. A method of producing ethylene glycol, comprising culturing the cell of claim 20 in the presence of xylose under conditions that result in the production of ethylene glycol.

22. An engineered bacterial cell that comprises a deletion of a gene encoding xylulokinase and a deletion of a gene encoding aldehyde dehydrogenase A.

23. The cell of claim 22, wherein the cell is an *Escherichia coli* cell.

24. The cell of claim 22 that further comprises a gene encoding an enzyme that interconverts xylulose and ribulose.

25. The cell of claim 24, wherein the enzyme that interconverts xylulose and ribulose is D-tagatose 3-epimerase.

26. The cell of claim 25, wherein the cell is an *Escherichia coli* cell.

* * * * *

SEQUENCE LISTING

```
<160> NUMBER OF SEQ ID NOS: 8

<210> SEQ ID NO 1
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 1
gctgccatgg acaaagttgg tatgttctac acc                           33

<210> SEQ ID NO 2
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 2
agtcgtcgac atgagctccg taggccggcc taaacgaatt cttaggccag tttatcacgg    60

<210> SEQ ID NO 3
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 3
gaattcgttt agagctctaa ataaggagga ataaccatgg tatccggcta tattgcagga    60
g                                                                    61

<210> SEQ ID NO 4
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 4
actggtcgac gctatcttca cacttcctct ataaattc                      38

<210> SEQ ID NO 5
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 5
ctgcggccgg ccctttaata aggagatata ccatggaacg aaataaactt gc        52

<210> SEQ ID NO 6
<211> LENGTH: 43
<212> TYPE: DNA
<213> ORGANISM: Artificial Sequence
```

```
<220> FEATURE:
<223> OTHER INFORMATION: Synthetic Oligonucleotide

<400> SEQUENCE: 6
gccggagctc taaacgaatt cttaccaggc ggtatggtaa agc            43

<210> SEQ ID NO 7
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 7
gctgccatgg agaacagcgc tttgaaagc                            29

<210> SEQ ID NO 8
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 8
ctatgagctc cgtaggccgg cctaaacgaa ttcttattcg acgttcagcg cgtc    54
```